US011642069B2

(12) United States Patent
Bergold et al.

(10) Patent No.: US 11,642,069 B2
(45) Date of Patent: May 9, 2023

(54) DIAGNOSIS OF MILD TRAUMATIC BRAIN INJURY

(71) Applicant: THE RESEARCH FOUNDATION FOR THE STATE UNIVERSITY OF NEW YORK, Albany, NY (US)

(72) Inventors: Peter John Bergold, Brooklyn, NY (US); William Winzer Lytton, Scarsdale, NY (US); Joshua Michael Skolnick, Far Rockaway, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 421 days.

(21) Appl. No.: 15/579,559

(22) PCT Filed: Jun. 3, 2016

(86) PCT No.: PCT/US2016/035871
§ 371 (c)(1),
(2) Date: Dec. 4, 2017

(87) PCT Pub. No.: WO2016/197029
PCT Pub. Date: Dec. 8, 2016

(65) Prior Publication Data
US 2018/0168499 A1      Jun. 21, 2018

Related U.S. Application Data

(60) Provisional application No. 62/171,198, filed on Jun. 4, 2015.

(51) Int. Cl.
*A61B 5/00* (2006.01)
*A61B 5/16* (2006.01)
*A61B 5/055* (2006.01)

(52) U.S. Cl.
CPC ............ *A61B 5/4064* (2013.01); *A61B 5/162* (2013.01); *A61B 5/055* (2013.01); *A61B 5/163* (2017.08); *A61B 2505/09* (2013.01)

(58) Field of Classification Search
None
See application file for complete search history.

(56) References Cited

U.S. PATENT DOCUMENTS 6,416,480 B1      7/2002   Nenov et al.
9,629,976 B1 *    4/2017   Acton ............... A61B 5/486
(Continued)

OTHER PUBLICATIONS

Mathias, et al. "Neuropsychological and Information Processing Performance and Its Relationship to White Matter Changes Following Moderate and Severe Traumatic Brain Injury: A Preliminary Study," 2004, Applied Neuropsychology, vol. 11, No. 3, 134-152 (Year: 2004).*

(Continued)

*Primary Examiner* — Alex M Valvis
*Assistant Examiner* — Aurelie H Tu
(74) *Attorney, Agent, or Firm* — Heslin Rothenberg Farley & Mesiti P.C.

(57) ABSTRACT

A stimulus is displayed in a visual field on a stimulus side (e.g., right or left) of a subject. An input is received from an input side of the subject. Where the input side is contralateral to the first stimulus side, a crossed reaction time is determined as a span of time between displaying the stimulus and receiving the input. Where the input side is ipsilateral to the stimulus side, an uncrossed reaction time is determined as a span of time between displaying the stimulus and receiving the input. A crossed-uncrossed difference time can be determined as a difference between the crossed reaction time and (Continued)

the uncrossed reaction time. The crossed reaction time, the uncrossed reaction time, and/or the crossed-uncrossed difference time can be used to determine a severity of Traumatic Brain Injury of the subject.

5 Claims, 20 Drawing Sheets

(56) References Cited

U.S. PATENT DOCUMENTS

| | | | |
|---|---|---|---|
| 2005/0165327 A1* | 7/2005 | Thibault | A61B 5/4076 600/558 |
| 2010/0092929 A1* | 4/2010 | Hallowell | G09B 7/00 434/167 |
| 2010/0094161 A1 | 4/2010 | Kiderman et al. | |
| 2010/0324443 A1 | 12/2010 | Ashton-Miller et al. | |
| 2012/0041330 A1* | 2/2012 | Prichep | A61B 5/4064 600/544 |
| 2013/0252215 A1* | 9/2013 | Wu | A61B 5/4088 434/236 |
| 2015/0094622 A1 | 4/2015 | Curtiss | |
| 2015/0177343 A1* | 6/2015 | Wald | A61B 5/0042 324/309 |
| 2016/0015289 A1 | 1/2016 | Simon et al. | |
| 2016/0073874 A1* | 3/2016 | Tsai | A61B 3/112 600/558 |
| 2021/0077006 A1* | 3/2021 | Salti | A61B 5/163 |

OTHER PUBLICATIONS

Reuter-Lorenz et al., "A split-brain model for Alzheimer's disease? Behavioral evidence for comparable intra and interhemispheric decline," Feb. 9, 2005, Elsevier, Neuropsychologia 43 (2005), 1307-1317 (Year: 2005).*

Peru, Andrea; Beltramello, Alberto; Moro, Valentina; Sattibaldi, Lorenzo; Berlucchi, Giovanni; Temporary and permanent signs of interhemispheric disconnection after traumatic brain injury; Pergamon; Neuropsychologia 41;pp. 634-643 (Year: 2003).*

Iacoboni, Marco; Zaidel, Eran; Crossed-uncrossed difference in simple reaction times to lateralized flashes: between- and within-subjects variability; Pergamon; Neuropsychologia 18; pp. 535-541 (Year: 2000).*

Miller et al., "Early Brain Injury in Premature Newborns Detected with Magnetic Resonance Imaging is Associated with Adverse Early Neurodevelopmental Outcome," Nov. 2005, The Journal of Pediatrics, vol. 147, Issue 5, pp. 609-616 (Year: 2005).*

Bergold; "Interhemispheric Information Transfer: A New Diagnostic Method for Mild Traumatic Brain Injury," DoD S&T Reports; Dated Oct. 2011, pp. 1-12.

Berlucci et al.; "Simple Reaction Times of Ipsilateral And Contralateral Hand To Lateralized Visual Stimuli," Brain, vol. 94, No. 3, Jan. 1, 1971; pp. 419-430.

Supplemental European Search Report dated Dec. 17, 2018, regarding EP16804584.

Written Opinion of the European Patent Office dated Dec. 17, 2018, regarding EP16804584.

International Search Report dated Sep. 14, 2016 for International Application No. PCT/US2016/035871, 11 pgs.

* cited by examiner

DIAGNOSIS OF MILD TRAUMATIC BRAIN INJURY

RELATED APPLICATION

This application claims priority to U.S. Provisional Application No. 62/171,198, filed Jun. 4, 2015, titled Diagnosis of Mild Traumatic Brain Injury, the entire contents of which are incorporated herein by reference.

GOVERNMENT LICENSE RIGHTS

This invention was made with government support under W81WH-10-1-1061 awarded by U.S. Army Research Acquisition Activity. The Government has certain rights to this invention.

BACKGROUND

Cognitive impairments commonly arise acutely after Mild Traumatic Brain Injury ("mTBI"). The impairments vary greatly in type, extent and persistence. Most mTBI patients spontaneously recover, yet approximately 20% develop long-lasting emotional, psychological and neurological problems termed post-concussive syndrome. The heterogeneity of outcomes raises major challenges to the prognosis and testing of therapies to treat mTBI. Prognostic biomarkers are critically needed to distinguish patients who will develop Post-Concussive Syndrome ("PCS") from those who spontaneously recover. The validation of prognostic biomarkers will improve treatment for the more than 22,000 service members who yearly receive an mTBI.

Mild TBI (e.g., Glasgow Coma Score>13) can be easily missed since its symptoms are either ignored or misdiagnosed as another neurological or psychological disease. Mild TBI most commonly damages white matter. These white matter regions include the corpus callosum, internal capsule, and cingulate. Diffusion Tensor-Magnetic Resonance Imaging (DT-MRI) is a highly sensitive brain imaging method to measure white matter injury; therefore, it has been shown to distinguish mTBI from other neurological or psychiatric disorders. MRI scanners needed for DT-MRI however, may be unavailable to subjects such as deployed troops; signifying a need for a simple, rapid mTBI screen that decides which soldiers need subsequent DT-MRI. White matter regions are frequently damaged by mTBI include the corpus callosum and other centroaxial structures that transfer information between the two cerebral hemispheres. The normal functioning of the corpus callosum and other white matter regions is assessed easily and rapidly using tests that rely upon interhemispheric information transfer ("IHT"). Deficits in IHT occur in moderate to severe TBI; however, these deficits have been studied less in mTBI.

SUMMARY

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, 8, 19, 20, 21, and/or 23. The other clauses can be presented in a similar manner.

Clause 1. A method, comprising:
displaying a stimulus in a visual field on a stimulus side of a subject, the visual field being a right visual field or a left visual field of the subject;
receiving an input, comprising an indication that the subject perceived the stimulus, from an input side of the subject, the input side being contralateral to the stimulus side;
measuring a crossed reaction time comprising a span of time between displaying the stimulus and receiving the input; and
based on the crossed reaction time, determining a severity of a Traumatic Brain Injury of the subject.

Clause 2. The method of clause 1, further comprising:
displaying a second stimulus in a second visual field on a second stimulus side of the subject, the second visual field being the right visual field or the left visual field of the subject;
receiving a second input, comprising an indication that the subject perceived the second stimulus, from a second input side of the subject, the second input side being ipsilateral to the second stimulus side;
measuring a crossed-uncrossed difference time as a difference between (i) the crossed reaction time and (ii) an uncrossed reaction time comprising a second span of time between displaying the second stimulus and receiving the second input; and
based on the crossed-uncrossed difference time, determining a severity of a Traumatic Brain Injury of the subject.

Clause 3. The method of clause 1, wherein determining the severity of the Traumatic Brain Injury comprises comparing the crossed reaction time to a crossed reaction time of a control subject not having Traumatic Brain Injury.

Clause 4. The method of clause 1, further comprising: outputting to an output device the determined severity of Traumatic Brain Injury.

Clause 5. The method of clause 1, further comprising: outputting to an output device a recommendation for a treatment based on the determined severity of Traumatic Brain Injury.

Clause 6. The method of clause 1, further comprising: treating the subject based on the determined severity of Traumatic Brain Injury.

Clause 7. The method of clause 4, wherein treating the subject comprises administering a drug to the patient, performing surgery on the patient, or applying a stimulus to the brain of the subject.

Clause 8. A method, comprising:
displaying a first stimulus in a first visual field on a first stimulus side of a subject, the first visual field being a right visual field or a left visual field of the subject;
receiving a first input, comprising an indication that the subject perceived the first stimulus, from a first input side of the subject, the first input side being contralateral to the first stimulus side;
displaying a second stimulus in a second visual field on a second stimulus side of the subject, the second visual field being the right visual field or the left visual field of the subject;
receiving a second input, comprising an indication that the subject perceived the second stimulus, from a second input side of the subject, the second input side being ipsilateral to the second stimulus side;
measuring a crossed-uncrossed difference time as a difference between (i) a crossed reaction time comprising a first span of time between displaying the first stimulus and receiving the first input and (ii) an uncrossed reaction time comprising a second span of time between displaying the second stimulus and receiving the second input; and based on the crossed-uncrossed difference time, determining a severity of a Traumatic Brain Injury of the subject.

Clause 9. The method of clause 8, wherein the first visual field and the second visual field are a same visual field.

Clause 10. The method of clause 8, wherein the first visual field and the second visual field are different visual fields.

Clause 11. The method of clause 8, wherein the first input side and the second input side are a same side of the subject.

Clause 12. The method of clause 8, wherein the first input side and the second input side are different sides of the subject.

Clause 13. The method of clause 8, wherein determining the severity of the Traumatic Brain Injury comprises comparing the crossed-uncrossed difference time to a crossed-uncrossed difference time of a control subject not having Traumatic Brain Injury.

Clause 14. The method of clause 8, wherein, in response to the first stimulus, the first input from the first input side contralateral to the first stimulus side is the only input available to the subject.

Clause 15. The method of clause 8, wherein, in response to the second stimulus, the second input from the second input side ipsilateral to the second stimulus side is the only input available to the subject.

Clause 16. The method of clause 8, wherein the right visual field and the left visual field are within a retina of the subject.

Clause 17. The method of clause 8, further comprising: treating the subject based on the determined severity of Traumatic Brain Injury.

Clause 18. The method of clause 17, wherein treating the subject comprises administering a drug to the patient, performing surgery on the patient, or applying a stimulus to the brain of the subject.

Clause 19. A method, comprising:

treating a subject for Traumatic Brain Injury, wherein a severity of the Traumatic Brain Injury is determined by:

displaying a stimulus in a visual field on a stimulus side of the subject, the visual field being a right visual field or a left visual field of the subject;

receiving an input, comprising an indication that the subject perceived the stimulus, from an input side of the subject, the input side being contralateral to the stimulus side;

measuring a crossed reaction time comprising a span of time between displaying the stimulus and receiving the input; and based on the crossed reaction time, determining the severity of the Traumatic Brain Injury of the subject.

Clause 20. A method, comprising:

treating a subject for Traumatic Brain Injury, wherein a severity of the Traumatic Brain Injury is determined by:

displaying a first stimulus in a first visual field on a first stimulus side of the subject, the first visual field being a right visual field or a left visual field of the subject;

receiving a first input, comprising an indication that the subject perceived the stimulus, from a first input side of the subject, the first input side being contralateral to the first stimulus side;

displaying a second stimulus in a second visual field on a second stimulus side of the subject, the second visual field being the right visual field or the left visual field of the subject;

receiving a second input, comprising an indication that the subject perceived the stimulus, from a second input side of the subject, the second input side being ipsilateral to the second stimulus side;

measuring a crossed-uncrossed difference time as a difference between (i) a crossed reaction time comprising a first span of time between displaying the first stimulus and receiving the first input and (ii) an uncrossed reaction time comprising a second span of time between displaying the second stimulus and receiving the second input; and based on the crossed-uncrossed difference time, determining the severity of a Traumatic Brain Injury of the subject.

Clause 21. A system, comprising:

a display module, configured to display a stimulus in a visual field on a stimulus side of a subject, the visual field being a right visual field or a left visual field of the subject;

an input module, configured to receive an input, comprising an indication that the subject perceived the stimulus, from an input side of the subject, the input side being contralateral to the stimulus side; and a determining module, configured to:
measure a crossed reaction time comprising a span of time between displaying the stimulus and receiving the input; and
determine, based on the crossed reaction time, a severity of a Traumatic Brain Injury of the subject.

Clause 22. The system of clause 21, wherein the input module consists of only one input device on the input side of the subject.

Clause 23. A system, comprising:

a display module, configured to display:
a first stimulus in a first visual field on a first stimulus side of a subject, the first visual field being a right visual field or a left visual field of the subject;
a second stimulus in a second visual field on a second stimulus side of the subject, the second visual field being the right visual field or the left visual field of the subject;

an input module, configured to receive:
a first input, comprising an indication that the subject perceived the first stimulus, from a first input side of the subject, the first input side being contralateral to the first stimulus side;
a second input, comprising an indication that the subject perceived the second stimulus, from a second input side of the subject, the second input side being ipsilateral to the second stimulus side;

a determining module, configured to:
measure a crossed-uncrossed difference time as a difference between (i) a crossed reaction time comprising a first span of time between displaying the first stimulus and receiving the first input and (ii) an uncrossed reaction time comprising a second span of time between displaying the second stimulus and receiving the second input; and
determine, based on the crossed-uncrossed difference time, a severity of a Traumatic Brain Injury of the subject.

Clause 24. The system of clause 21, wherein the input module consists of only one input device on the input side of the subject.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are exemplary and explanatory and are intended to provide further explanation of the subject technology as claimed.

BRIEF DESCRIPTION OF THE DRAWINGS

The accompanying drawings, which are included to provide further understanding of the subject technology and are incorporated in and constitute a part of this description, illustrate aspects of the subject technology and, together with the specification, serve to explain principles of the subject technology.

DETAILED DESCRIPTION

In the following detailed description, specific details are set forth to provide an understanding of the subject technology. It will be apparent, however, to one ordinarily skilled in the art that the subject technology may be practiced without some of these specific details. In other instances, well-known structures and techniques have not been shown in detail so as not to obscure the subject technology.

Some aspects of the subject technology relate to obtaining data regarding peripheral reaction time. In some embodiments, the peripheral reaction time is measured and/or determined as the interval between the appearance of the visual stimulus and the input from the subject. Some aspects of the subject technology relate to using such data to diagnose and stratify mTBI patients. Presently methods for diagnosing mTBI lack accuracy and specificity. Methods under development include: DT-MRI, electroencephalography, and neuropsychological tests. The inventors made the discovery that a majority of mTBI patients have deficits in peripheral reaction times that are greater than two standard deviations than controls. Over 20% of mTBI patients have large deficits in peripheral reaction time that are greater than 10 standard deviations from the controls. Peripheral reaction time was able to stratify patients based upon white matter abnormalities as seen with DT-MRI or with neuropsychological testing. Peripheral reaction time can be either uncrossed ("URT") or crossed ("CRT"). For example, in a right hand dominant individual, URT is measured using stimuli on the right peripheral field and CRT is measured using stimuli on the left peripheral field. This is reversed in a left-handed individual. The difference between CRT and URT is the crossed-uncrossed difference ("CUD"). CUD deficits were highly correlated with radiological deficits in the posterior corpus callosum and left cortical spinal tract as seen using DT-MRI. Determinations using the peripheral reaction time test can occur acutely after injury or after a longer time span has passed.

Figure 10A:
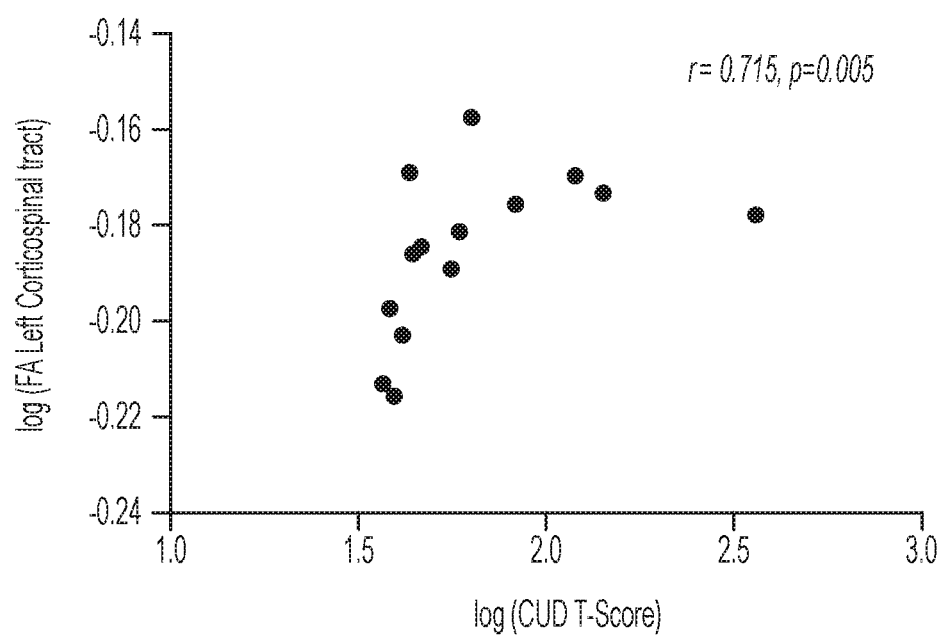
FIG. 10A illustrates a significant correlation between FA in the left corticospinal tract and CUD T-Scores.
Figure 10B:
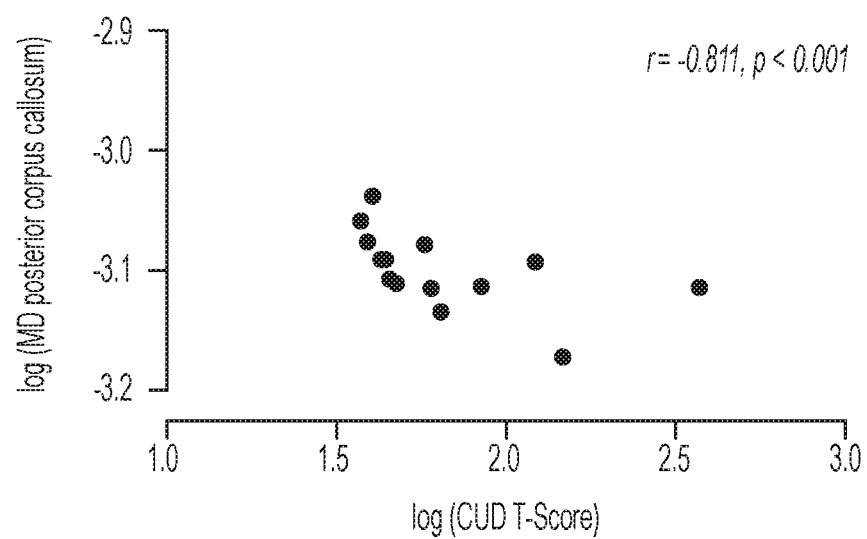
FIG. 10B illustrates a significant correlation between MD in the posterior corpus callosum and CUD T-Scores.

Some aspects of the subject technology relate to tests to diagnose mTBI based on the difference between the crossed and uncrossed reaction time. Some aspects are based on the understanding that the most vulnerable structures to head trauma is white matter, in particular, the corpus callosum that connects the two cerebral hemispheres. The crossed-uncrossed difference was previously thought to be a surrogate marker for the integrity of the corpus callosum; and the methods of the subject technology have shown that the integrity of the corpus callosum correlated with crossed-uncrossed reaction time (FIGS. 10A-B). The mTBI patients had white matter damage that did not localize to any particular brain region. A large majority of the patients had deficits in peripheral reaction time even though white damage was not localized. This suggested that peripheral reaction time was slowed by damage to a variety of centroaxial white matter tracts.

A minority of patients with mTBI have modest deficits on simple reaction time tests. Some aspects of the subject technology involve measurement of reaction time in a way that reveals much larger deficits in a much large cohort of patients. Patients with large reaction time deficits also had greater white matter injury and performed more poorly on neuropsychological testing. Thus, measurements of reaction time based on aspects of the subject technology can stratify patients based upon radiological and functional measurements of brain damage.

Figure 1A:
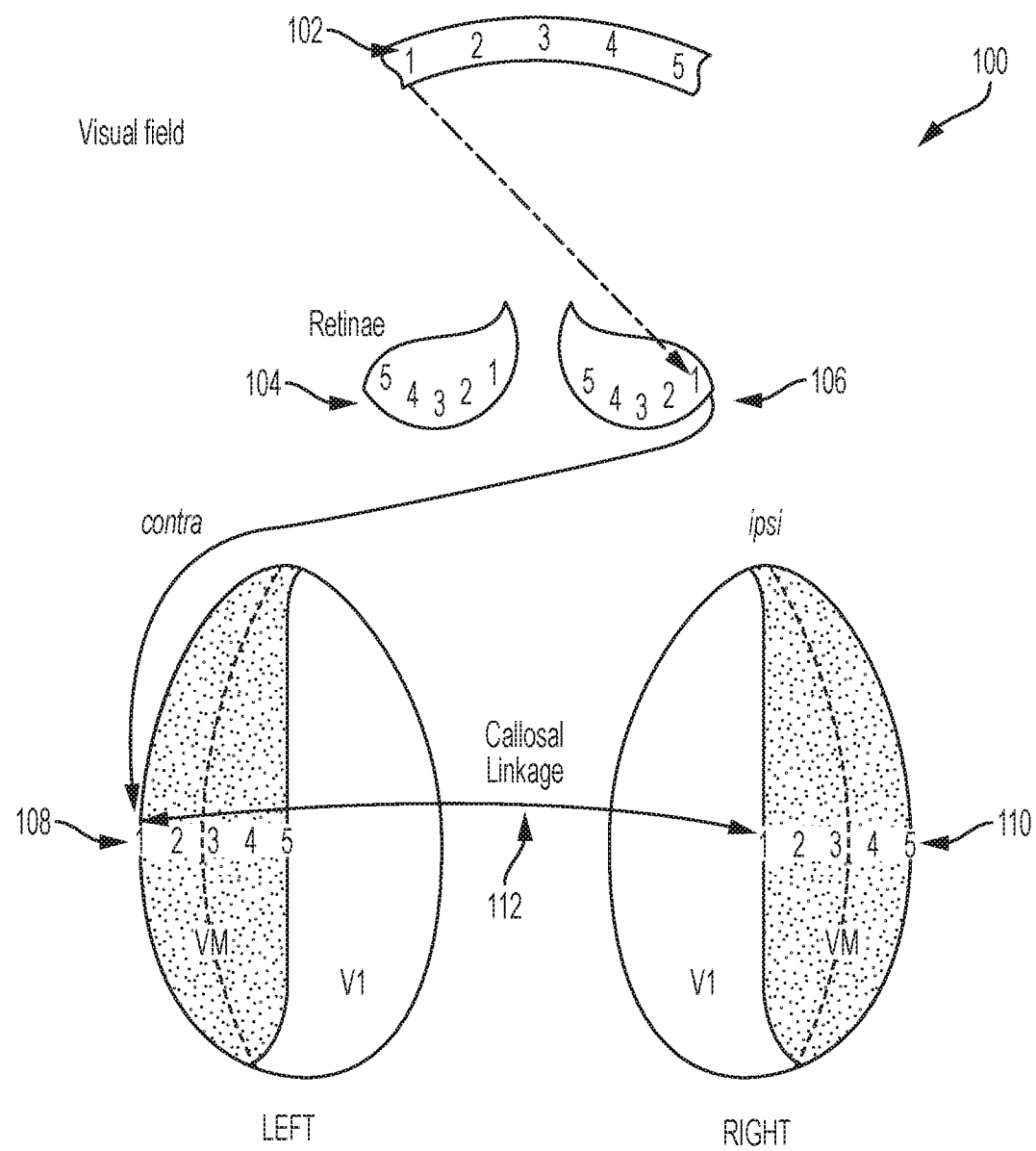
FIG. 1A illustrates an Interhemispheric information transfer (IHT) test in accordance with an embodiment of the disclosed subject matter.
Figure 1B:
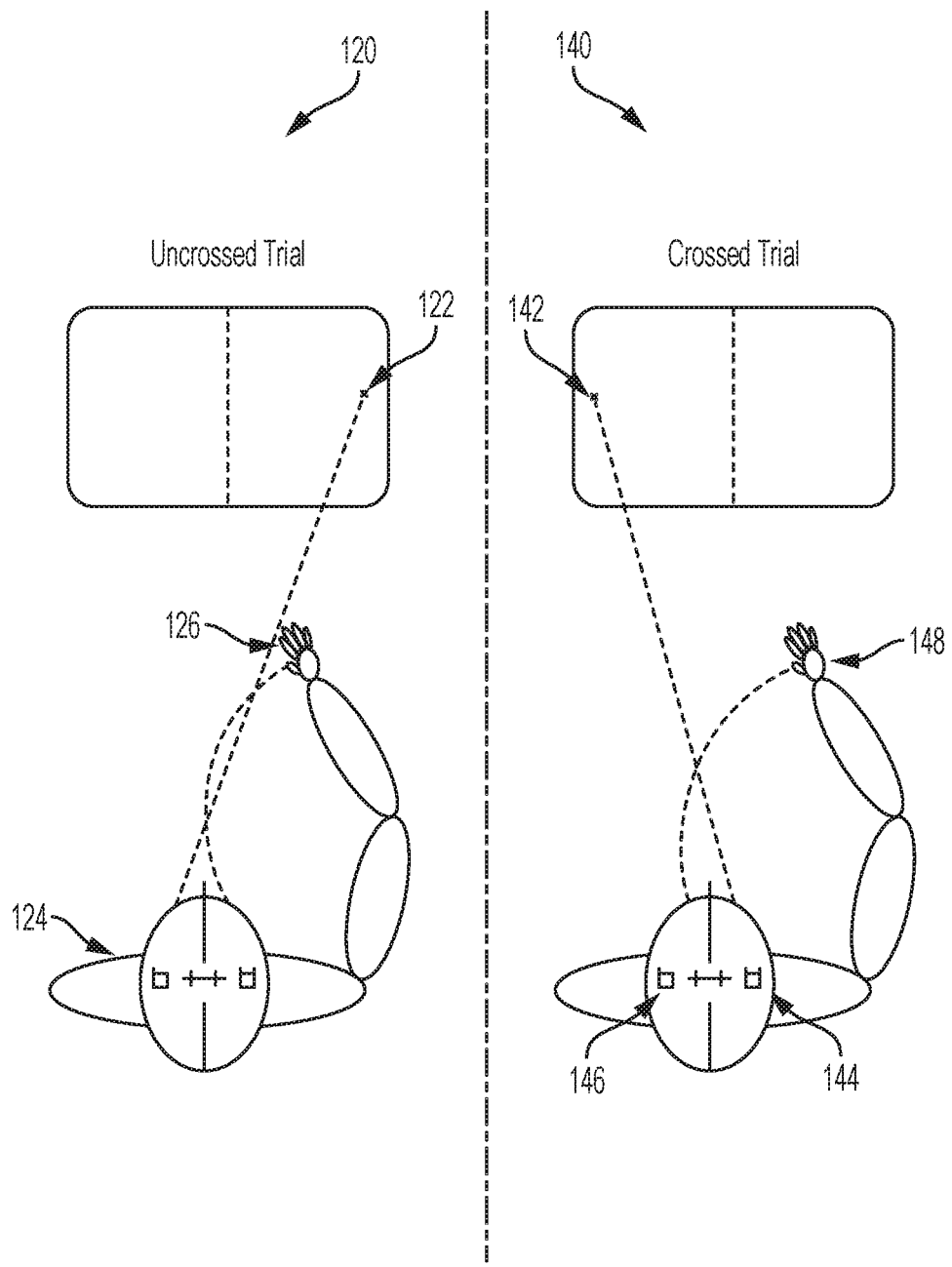
FIG. 1B illustrates a summary of the IHT test in control patients in accordance with an embodiments of the disclosed subject matter.
Figure 1C:
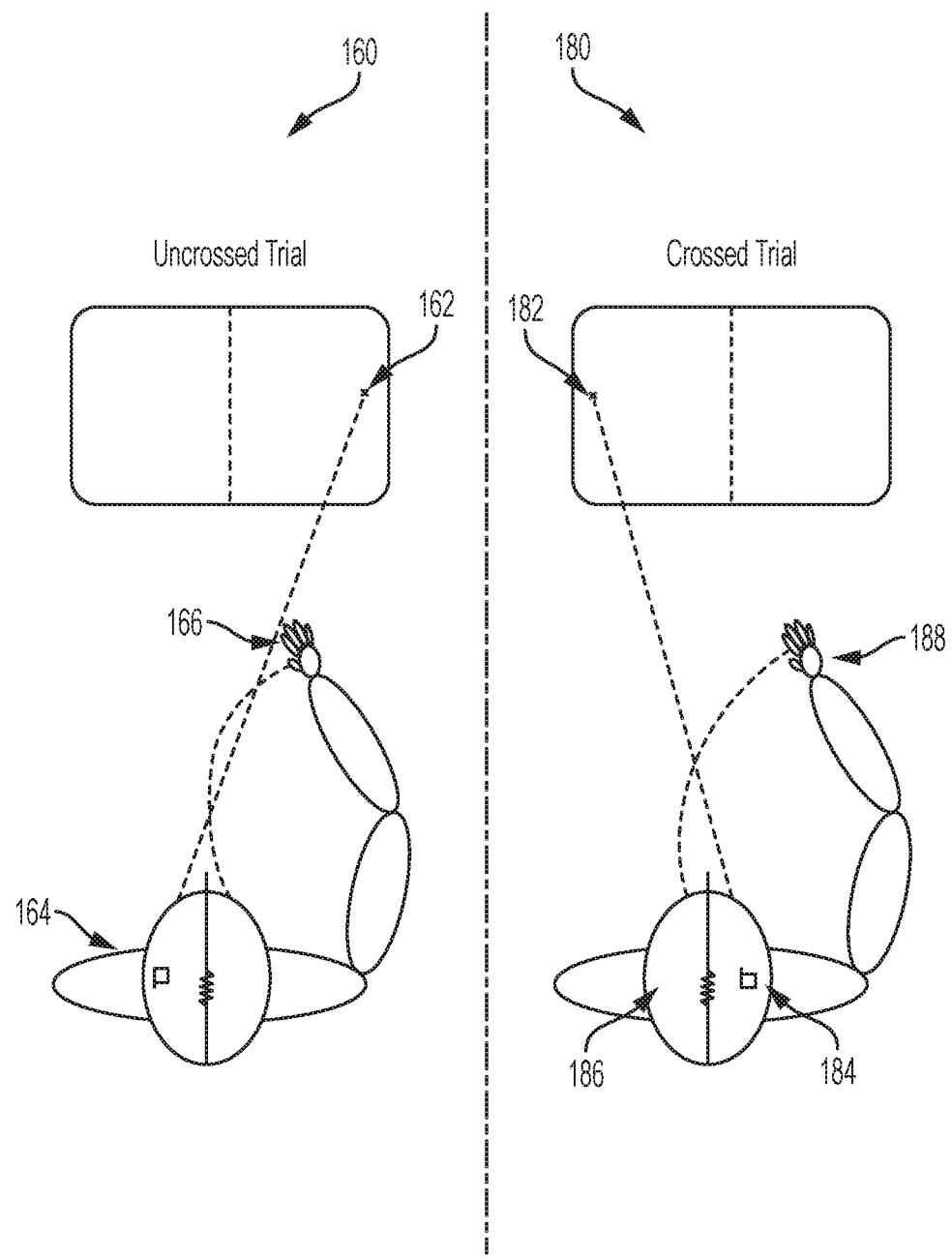
FIG. 1C illustrates a summary of the IHT test in mTBI patients in accordance with an embodiment of the disclosed subject matter.

Some aspects of the subject technology relate to measurement of interhemispheric information transfer using software programs and supporting hardware. According to some embodiments, the nose of the subject is placed a given distance from a location on a display. The subject fixates on a point (e.g., center) on the display while placing his/her hand (e.g., dominant hand) on an input device. A dominant or non-dominant hand may be used. The subject hits the space bar upon registering the appearance of a visual stimulus a given distance (e.g., 31.6°) to the left or right from the point of focus. The visual stimulus remains on the screen until an input to the input device is provided by the patient (FIGS. 1A-C). The time that the visual stimulus appears can randomly vary, to minimize prediction and anticipation by the patient.

Some aspects of the subject technology relate to use of reaction times to visual stimuli to assess oculomotor function in patients with mTBI. Control of eye movements by the brain are complex because they are controlled by many brain regions (e.g., the lateral intraparietal area, the frontal eye fields, the supplementary eye fields and the dorsolateral prefrontal cortex, the basal ganglia, superior colliculus, the reticular formation and the oculomotor vermis and the fastigial oculomotor regions of the cerebellum). Due to the fact that many brain regions must coordinate their activity, eye movement impairments are common in traumatic brain injury. Sophisticated eye trackers track eye actions directly to precisely measure eye movements. An alternative approach is to measure reaction time as an indirect measure of oculomotor function. These two tests appear similar yet can result in different outcomes, suggesting that the tests are measuring different aspects of brain function that control eye movements.

Figure 2:
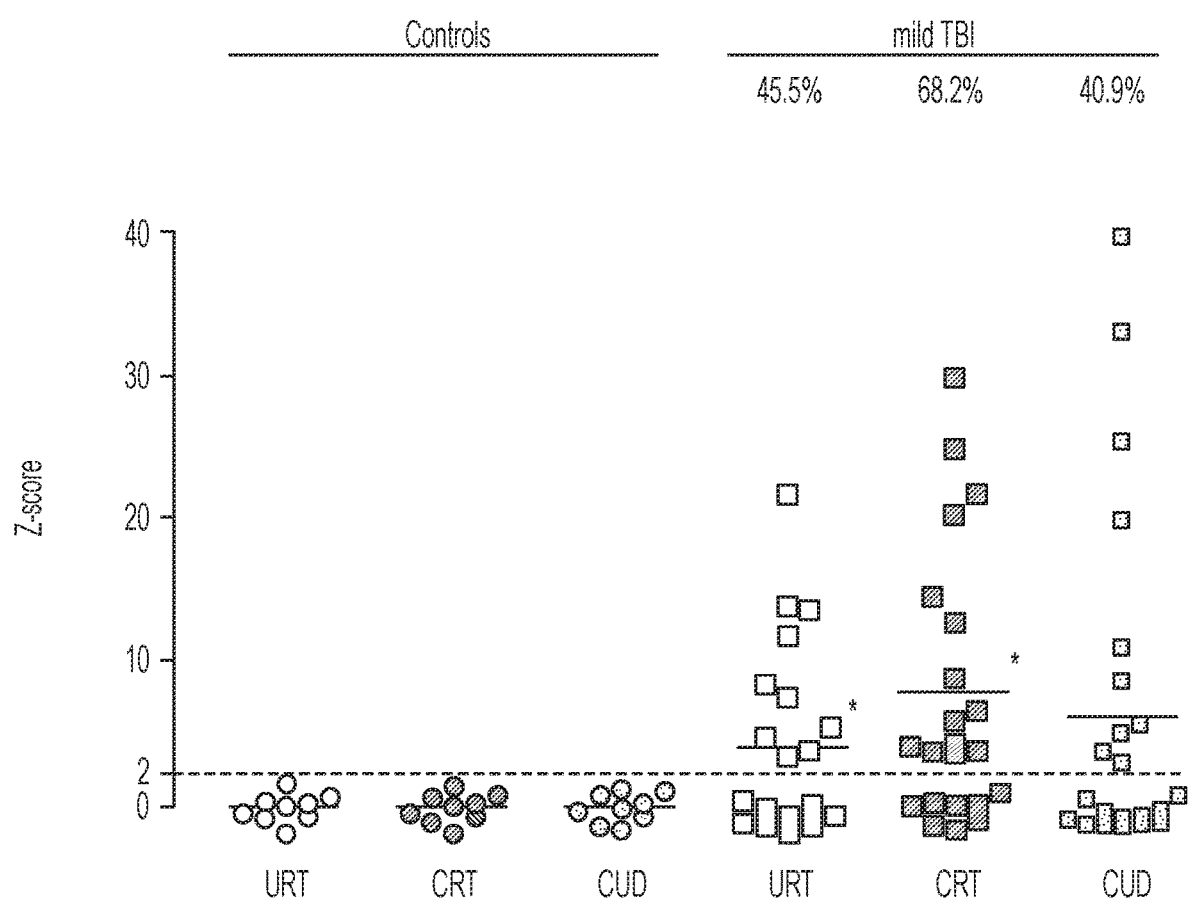
FIG. 2 illustrates reaction times of control and mTBI patients on IHT test in accordance with an embodiment of the disclosed subject matter.

Some aspects of the subject technology relate to use of peripheral vision tests for measuring reaction times for subjects. Some aspects of the subject technology relate to using URT of a peripheral vision task (FIG. 2). In tests performed, the comparison of URTs for known uninjured patients and known mildly injured patients demonstrated significant distinctions between the two groups, indicating a useful indicia for determining the presence and/or severity of TBI.

The results suggest that tests of the subject technology assess a deficit distinct from 2-choice compatible reaction time tests. Some aspects of the subject technology relate to measurement based on the distance traveled by the eye during testing. Some aspects of the subject technology relate to a simplified test that reveals more significant differences between the control and injured groups.

EXAMPLES

One hypothesis of this subject matter is that mTBI produces IHT deficits and that neuropsychological tests employing IHT can be an initial field screen for mTBI. A demonstration that IHT provides an initial screen for mTBI potentially has a large and immediate impact on military health. This hypothesis is tested by determining whether a neuropsychological test employing IHT can be an initial screen for mTBI in humans.

22 injured and 9 controls were recruited at Parkland Hospital, Dallas Tex. between February, 2011 and January, 2014. All were aged 18-50 years with a Glasgow Coma Score≥13. The patient's chart was reviewed for information about the nature of the injury and his/her first post-resuscitation Glasgow Coma Scale. Upon determining that the patient was eligible, consent was obtained from the patient or from a legally authorized representative according to the local IRB regulations for informed consent. Eligible TBI subjects were under the care of the Department of Neurosurgery, the Department of Physical Medicine and Rehabilitation. They were consented face-to face by investigators, study manager, or a research assistant. Healthy controls were age and gender-matched family members of the TBI patients or other healthy volunteers who agree to participate in the study. They were provided detailed information about the study, their commitment to the study, as well as a copy of the consent form that they signed. All 22 patients and controls received the IHT test within 24 hours after injury. Of the 22 patients consented, 14 injured patients received MRI scans within one week of injury. Of the remainder, 6 of these patients left the hospital after being consented and receiving the IHT, but did not return for their scheduled appointment for scanning and could not be contacted. One patient voluntarily left the study and one could not be scanned since the MRI was not working properly. All nine controls were scanned.

Consent was obtained from the participant once they become competent to grant consent. All patients included in the study were alert, oriented, and able to follow commands by a nurse. The level of awareness and orientation of the patient was further confirmed the experimenter present. All patients were able to sit up, adjust, and complete the trial in entirety without problem. All tests were done only if the patient presented well. Participation in other observational or treatment trials of TBI was not an exclusion criterion for enrollment into the current study. While this has a small potential to introduce some ambiguity into our study, we believe that this risk is small compared to the expected practical and scientific benefits.

Subjects were paid $100.00 for each magnetic resonance imaging (MM) session with neuropsychological testing they undergo. Study participants had an MM within 7 days of their injury and, either on the same day or a different day, had neuropsychological testing done by a neuropsychologist on our staff. Participants are paid $100 (check or gift card) if they completed both the MRI and testing. If they did not complete an MRI procedure (e.g. due to claustrophobia while in the scanner), or they wanted to stop the neuropsychological interview due to fatigue or emotional upset, they were paid a prorated amount, depending on the task attempted or completed. They were paid $50.00 for: (1) attempting the scan, (2) attempting to do the MRI, becoming claustrophobic and had to exit the scanner or (3) they did not complete the imaging nor did they have neuropsychological testing. If they completed the MRI but not the neuropsychological testing, they were paid for the MRI ($50.00). They received the full $100.00 if they did the MM and attempted the testing.

Both mTBI patients and controls were scanned using a 3 tesla magnet MM at the Advanced Imaging Research Center at University of Texas Southwestern Medical Center. Total time to complete each MM was an hour or less. At no stage of the study were IV's, shots or injections, restraints required. All research-related MRI studies were performed at no cost to the subject. Research-related MRI's were made available to the patient's treating physician unless requested by the patient, since the sole reason for doing the MRI was research. If the patient requested a copy of the MRI, a digital disc was provided to the patient or his physician.

Nine control patients and 22 patients with putative mTBI received a test of IHT, as shown in Table 1, below:

TABLE 1

The control and injured groups were matched for age, handedness and sex, but not for education. Educational level was controlled in the neuropsychological testing.

|  | Control | Injured | Statistic |
|---|---|---|---|
| Age | 33.5 ± 2.6 | 32.3 ± 1.6 | t30 = 0.17, p > 0.5 |
| Years of education | 12.4 ± 0.5 | 16.0 ± 0.6 | t30 = 5.53, p < 0.01 |
| % left handed | 11.1 | 18.2 | X2 = 0.83, p > 0.5 |
| % female | 33.3% | 22.7% |  |

Criteria for inclusion or exclusion of experimental subjects are shown in Table 2, below:

TABLE 2

Criteria for inclusion or exclusion of experimental subjects.

| Inclusion Criteria | Exclusion Criteria |
|---|---|
| Post-resuscitation Glasgow Coma Score ≥13 | History of pre-existing neurologic disease (epilepsy, brain tumors, meningitis, cerebral palsy, encephalitis, brain abscesses, vascular malformations, cerebrovascular disease, Alzheimer's disease, multiple sclerosis, or HIV-encephalitis) |
| Injury mechanism compatible with mTBI Enrollment within 7 days of injury | |
| Reasonable expectation for completion of outcome measures | History of a premorbid disabling condition that interfere with outcome assessments |
| Residence inside the United States | Previous hospitalization for TBI >1 day |
| Age 18-50 years inclusive | Contraindication to MRI (i.e. incompatible metal implants) Membership in a vulnerable population (prisoner) Pregnancy |

Inclusion criteria for healthy controls:
1. Good general health
2. Ability to provide informed written consent
3. At least an 8th grade education or employed to demonstrate that participant is not cognitively impaired
4. Normal brain anatomy on magnetic resonance imaging (MRI)
5. Ability to speak either English or Spanish.

Exclusion criteria for healthy controls:
1. Abnormal medical history such as neurological disease including head trauma with loss of consciousness
2. Having a contraindication to MRI such as pregnancy, breast-feeding, surgical clips, metallic artificial prostheses, surgically implanted pacemakers, or claustrophobia.

The same day or on another day that was convenient to the study participant, a neuropsychologist administered the IHT neuropsychological battery, using a laptop computer running tachistoscopic software that displayed a plus sign to either the left visual field or right visual field of the retina. In the IHT test, the subject placed his/her hand (e.g., dominant hand) on the space bar. The computer recorded the time needed to between projecting the plus sign and the activation of the space bar. Uncrossed reaction time (URT) was defined as the time elapsed was recorded between the projection of the plus sign to the hemiretinal field ipsilateral to the response hand and the activation of the space bar. Crossed reaction time (CRT) was defined as time elapsed was recorded between the projection of the plus sign to the hemiretinal field contralateral to the response hand and the activation of the space bar. Interhemispheric transfer time (ITT) was defined as the difference between the uncrossed and crossed reaction times. ITT was predicted to be slower in patients with mTBI as compared to control patients.

FIG. 1A illustrates an IHT test in accordance with an embodiment of the disclosed subject matter. In FIG. 1A, an environment 100 for the IHT test includes visual field 102, left hemiretina 104, right hemiretina 106, left cerebral hemisphere 108, right cerebral hemisphere 110, and callosal linkage 112. A peripheral stimulus can be selectively detected by one hemiretina. From the hemiretina the stimulus enters the contralateral visual cortex and then transferred to the ipsilateral visual cortex via callosal linkage/corpus callosum. For example, a stimulus in the visual filed 102 can be detected by right hemiretina 106; from the right hemiretina 106 the stimulus enters the contralateral visual cortex located in the left cerebral hemisphere 108 and then transferred to the ipsilateral visual cortex located in the right cerebral hemisphere 110 via the callosal linkage 112. Callosal linkages were hypothesized to be function aberrantly after mTBI.

In some embodiments, IHT tests were performed using a laptop computer running software that displays visual stimuli exclusively to either the left visual field or right visual field of the retina. In some embodiments, the subject fixated on a central point on a laptop computer screen. The subject then perceived a visual stimulus placed either 31.6° to the left or right of the fixation point and pressed a computer key with his/her dominant hand. The stimulus remained on the screen until the key press. The test consisted of 50 trials that were randomized to side and intertrial interval. Reaction time was defines as the interval between the appearance of the stimulus and the key press. Peripheral reaction time was either an uncrossed (URT) or crossed (CRT) reaction time. In a right response hand individual, URT was measured using stimuli on the right peripheral field stimuli and CRT was measured using on the left peripheral field. The difference between CRT and URT was the crossed-uncrossed difference (CUD). The CUD was used as a surrogate measure of ITT.

The time between a visual stimulus and a hand response was measured in FIG. 1B and FIG. 1C. FIG. 1B illustrates an IHT test in control patients in accordance with an embodiments of the disclosed subject matter. In the uncrossed trial, the peripheral stimulus is in the same hemisphere as the motor cortex controlling the hand while it is in the opposite hemisphere in the crossed trial. For example, in an uncrossed trial 120, a stimulus 122 can be detected by the visual cortex located in the left cerebral hemisphere 124. And the motor cortex controlling a hand 126 is also located in the left cerebral hemisphere 124. In a crossed trial 140, a stimulus 142 can be detected by the visual cortex located in the right cerebral hemisphere 144. And the motor cortex controlling a hand 148 is located in the left cerebral hemisphere 146, which is the opposite cerebral hemisphere from the right cerebral hemisphere 144.

FIG. 1C illustrates an IHT test in mTBI patients in accordance with an embodiments of the disclosed subject matter. In the uncrossed trial, the peripheral stimulus is in the same hemisphere as the motor cortex controlling the hand while it is in the opposite hemisphere in the crossed trial. For example, in an uncrossed trial 160, a stimulus 162 can be detected by the visual cortex located in the left cerebral hemisphere 164. And the motor cortex controlling a hand 166 is also located in the left cerebral hemisphere 164. In a crossed trial 180, a stimulus 182 can be detected by the visual cortex located in the right cerebral hemisphere 184. And the motor cortex controlling a hand 188 is located in the left cerebral hemisphere 186, which is the opposite cerebral hemisphere from the right cerebral hemisphere 184.

One hypothesis of this study was that lowered FA in selected white matter regions is positively correlated with deficits in IHT test. This hypothesis was tested in two steps: 1) differences in neuroimaging parameters were determined between healthy controls and patients with mTBI. Four different DT-MRI-derived measures (whole brain white matter FA; region of interest FA measures (for 12 different ROIs) and tractography FA measures (for a total of 28 different tracts). Groups of three or more were analyzed by multiple analysis of variance. Subsequent comparison of two groups was done using Student-Neumann-Keuls post-hoc test. Groups of two were analyzed by Student's t test. The percent left-handed in the control and experimental groups were analyzed by chi-square analysis. In all tests, statistical significance was set at 0.05.

FIG. 2 illustrates reaction times of control and mTBI patients on IHT test in a scatter plot of the Z-scores in accordance with an embodiment of the disclosed subject matter. As discussed earlier, CUD was predicted to be a surrogate marker for ITT. CUD was predicted to be slower in patients with mTBI (FIG. 1C) than control patients (FIG. 1B). As shown in FIG. 2, similar reaction times were observed for CRT and URT in uninjured/control group, which is as anticipated. Deficits in CUD that are greater than 2 standard deviations (SD) were seen in 40.9% of patients. Deficits>2SD were seen in 68.2% and 45.5% of the patients in CRT and URT, respectively. These data suggest that visual deficits are widespread for they were seen in 72.7% of all patients (FIG. 2). Whole voxel analysis of fractional anisotropy (FA) was similar between injured patients and uninjured controls. Whole voxel analysis was then repeated after stratifying the injured patients based upon CUD. Whole voxel FA in patients with CUD scores>2 standard deviations differed significantly (p<0.001) from patients with CUD scores<2SD. Whole voxel analysis was also performed for mean diffusivity (MD). Whole voxel analysis of MD in injured patients significantly differed than controls (p<0.01). Whole voxel MD in patients with CUD scores>2 standard deviations differed significantly from patients with CUD scores<2 standard deviations. These data strongly suggest that CUD predicts the severity of white matter damage seen with DT-MRI.

The CUD of the two groups did not significantly differ. The two groups had significantly difference. These data suggest that the CRT and URT, but not the CUD, of the injured patients significantly differed from controls. Z-scores of reaction times were computed. A scatter plot of the Z-scores of the data indicated differing scatter of the URT, CRT, and CUD of the injured and control groups. No control subject had a URT, CRT of CUD exceeding 2 standard deviations while scores exceeding two standard deviations were seen in 68.2%, 45.5%, and 40.9% of the URT, CRT, and CUD groups, respectively. The large scatter in the CRT and URT scores was expected since the injured and control groups differed. More interesting was the stratification of the CUD scores since the unstratified values did not differ. Therefore, the injured patients were separated post-hoc into two groups based upon CUD z-scores; one group with standard deviations<2 and a second group with standard deviations>2.

Both the injured and control subjects decreased both their URT and CRT throughout the 50 random trials. Surprisingly, both control and injured subjects had a similar change in URT per trial ((in msec/trial) control, $-2.90 \pm 1.27$; injured, $-4.92 \pm 2.86$, $t_{29}=-0.45$, $p>0.5$). The change in CRT was also similar ((in msec/trial) control, $-0.38 \pm 0.95$; injured, $-2.15 \pm 2.56$, $t_{29}=-0.43$, $p>0.5$). The change in CRT per trial was similar injured patients with a standard deviation of the CRT>2 ((in msec/trial)<2, $-6.23 \pm 3.80$, $t_{13}=-0.98$, $p>0.3$; >2, $-6.24 \pm 3.80$, $t_{23}=-0.27$, $p>0.5$). There was also no change in URT depending upon the size of the standard deviation ((in msec/trial)<2, $-0.90 \pm 1.58$, $t_{19}=0.64$, $p>0.5$; >2, $-5.81 \pm 5.22$, $t_{17}=-0.97$, $p>0.3$). These data suggest that injured and control patients retained similar ability to learn the task regardless of the size of their impairment.

Twelve of the mTBI patients also received a battery of neuropsychology tests that included: Processing speed index, Digit Symbol, Symbol Search, Digit Span, Controlled Oral Word Test, Trails A and B, Brief Symptom Inventory, Stroop 1 and 2, and California Verbal Learning Test. mTBI patients showed deficits in Processing speed index, Digit Span, Controlled Oral Word Test, Trails A, Stroop 1 and 2 and California Verbal Learning Test. Patients with CUD deficits>2 SD performed significantly worse than patients with CUD deficits<2 SD on Controlled Oral Word Test, Stroop 1, and the Obsessive Compulsive and Positive Symptoms subtests of the Total Basic Symptom Inventory. These data suggest that CUD deficits can stratify mTBI on particular neuropsychological tests. Taken together, these data suggest that CUD is a potential biomarker for mTBI severity and could be used as an initial screen for mTBI.

Figure 3:
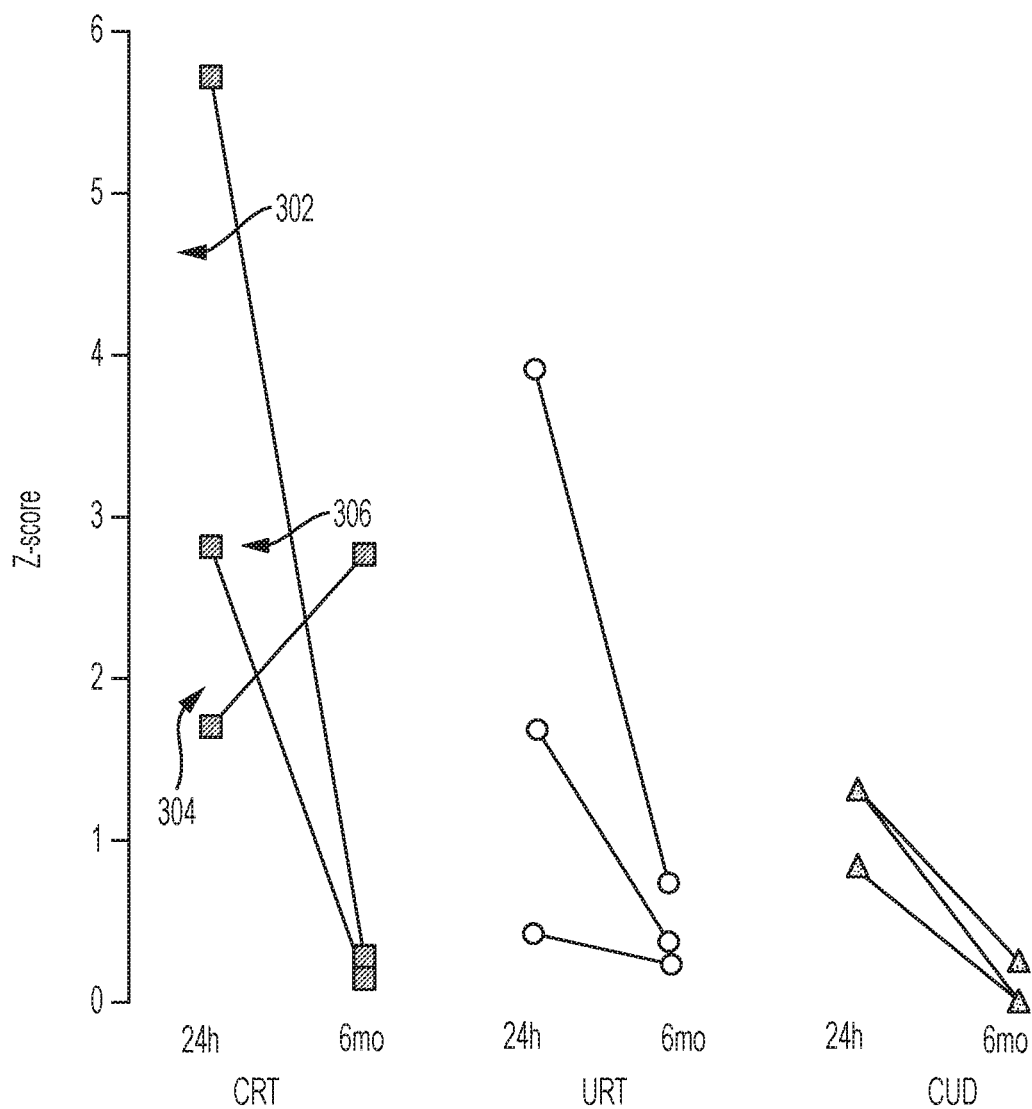
FIG. 3 illustrates a comparison of CRT, URT, and CUD at 24 hours and 6 months post-injury in accordance with an embodiment of the disclosed subject matter.

FIG. 3 illustrates a comparison of CRT, URT, and CUD at 24 hours and 6 months post-injury in accordance with an embodiment of the disclosed subject matter. Six months after injury, only 3 patients were retested on the IHT test. Two patients with CRT and URT>2 standard deviations at 24 h were no different from controls at 6 months (curves 302 and 304). The remaining patient had a CRT<2 standard deviations had a CRT>2 standard deviations at 6 months (curve 306). These data suggest the peripheral reaction time deficits can be long-lasting. A caveat of this finding is very few patients who received the IHT test six months after injury.

DT-MRI data from the control and injured patients were first analyzed using voxel-based analysis of FA and MD of the whole brain. This analysis has the advantage over the subsequent region of interest analyses since whole voxel analysis makes no prior assumption of the location of white matter damage. Whole voxel analysis has been particularly useful in the analysis of mTBI that produces a diffuse white matter injury. There were no significant differences in FA when comparing all mTBI patients and controls.

Figure 4:
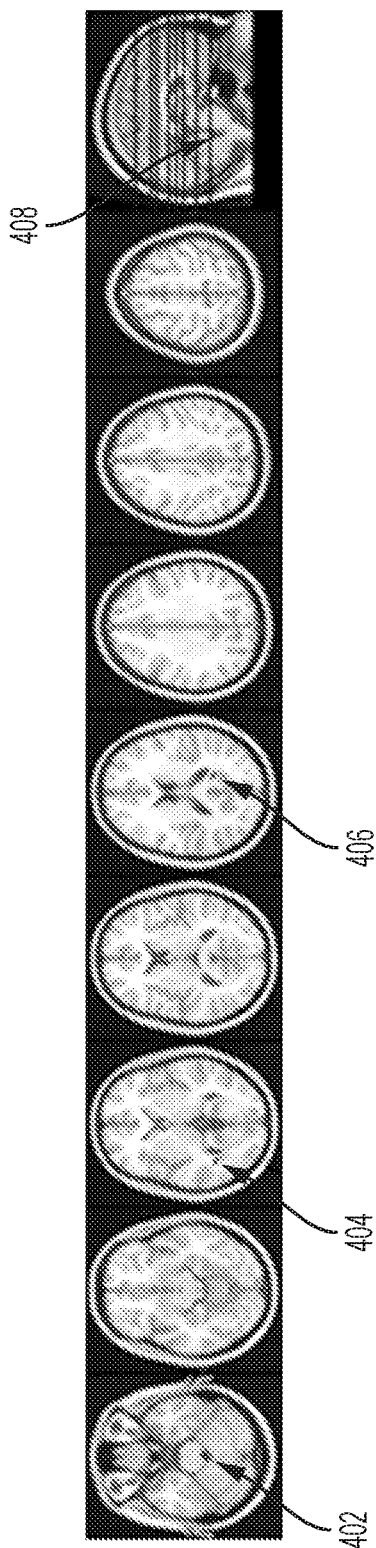
FIG. 4 illustrates DT-MRI whole voxel analysis of Fractional Anisotropy ("FA") of a patient of an mTBI patient with a CUD<2SD compared to a control subject.

FA was then further analyzed using the two injured groups based upon CUD z-scores. FIG. 4 illustrates DT-MRI whole voxel analysis of Fractional Anisotropy ("FA") of a patient of an mTBI patient with a CUD<2SD compared to a control subject. Voxels with FA that significantly differed from uninjured control are indicated as 402, 404, 406, and 408. This patient had 0.311% (258 out of 82,912) aberrant voxels.

Figure 5:
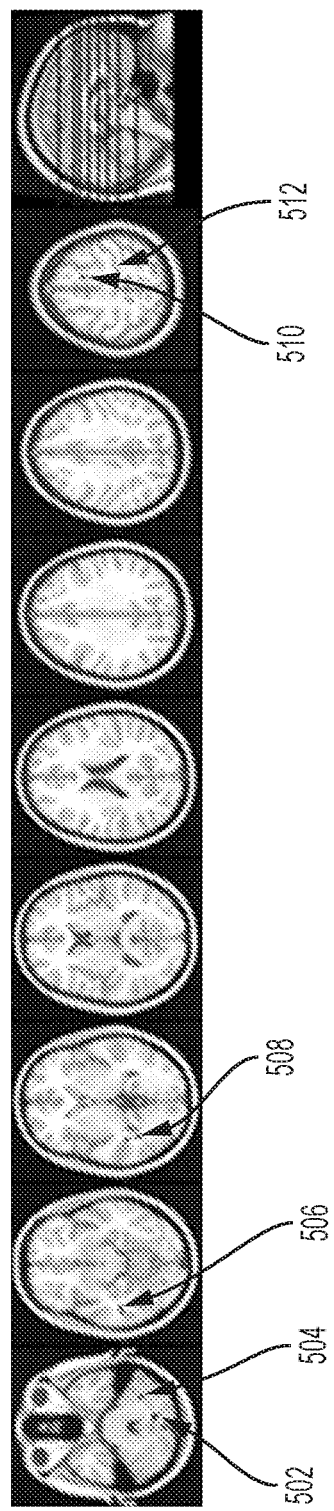
FIG. 5 illustrates DT-MRI whole voxel analysis of FA of a patient of an mTBI patient with a CUD>2SD compared to a control subject.

FIG. 5 illustrates DT-MRI whole voxel analysis of FA of a patient of an mTBI patient with a CUD>2SD compared to a control subject. Voxels with FA that significantly differed from uninjured control are indicated as 502, 504, 506, 508, 510, and 512. This patient had 0.364% (275 out of 75,382) aberrant voxels. Patients with a CUD<2SD had aberrant FA voxels clustering in the splenium (p<0.01).

Whole voxel FA in patients with CUD scores>2 standard deviations differed significantly from patients with CUD scores<2SD (p<0.01). Patients with CUD scores>2 standard deviations had voxels with significant FA differences clustered in the splenium, a sub-region of the corpus callosum (p<0.01 FIG. 5). Patients with CUD scores>2 standard deviations had FA values significantly different from uninjured controls (p<0.001). These data suggest that stratifying patients based upon CUD standard deviations selected a subpopulation of injured patients that has significant differences whole brain FA than both uninjured controls and patients with a standard deviation<2.

Figure 6:
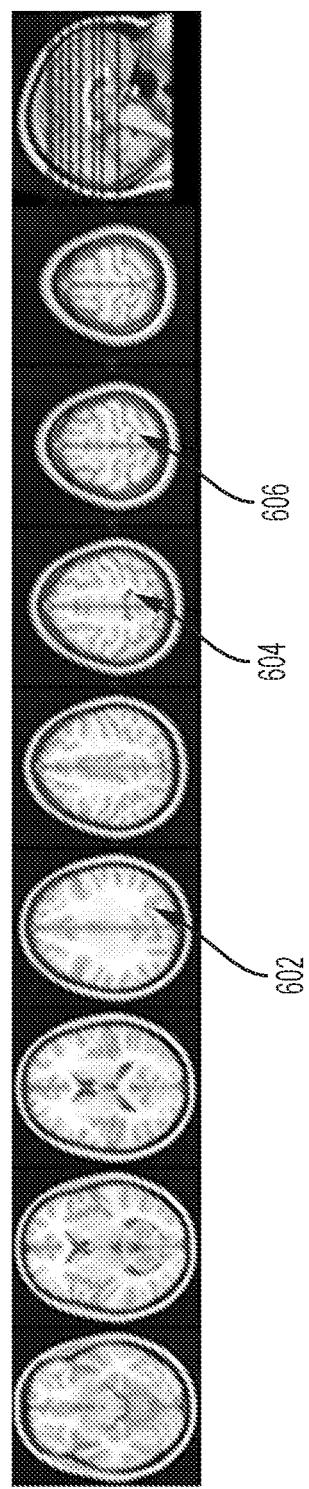
FIG. 6 illustrates DT-MRI whole voxel analysis of Mean Diffusivity ("MD") of a patient of an mTBI patient with a CUD<2SD compared to a control subject.

MD was also analyzed using whole voxel analysis was repeated in the injured and control cohort. FIG. 6 illustrates DT-MRI whole voxel analysis of Mean Diffusivity ("MD") of a patient of an mTBI patient with a CUD<2SD compared to a control subject. Voxels with MD that significantly differed from uninjured control are indicated as 602, 604, and 606. This patient had 0.053% (57 out of 108,423) aberrant voxels.

Figure 7:
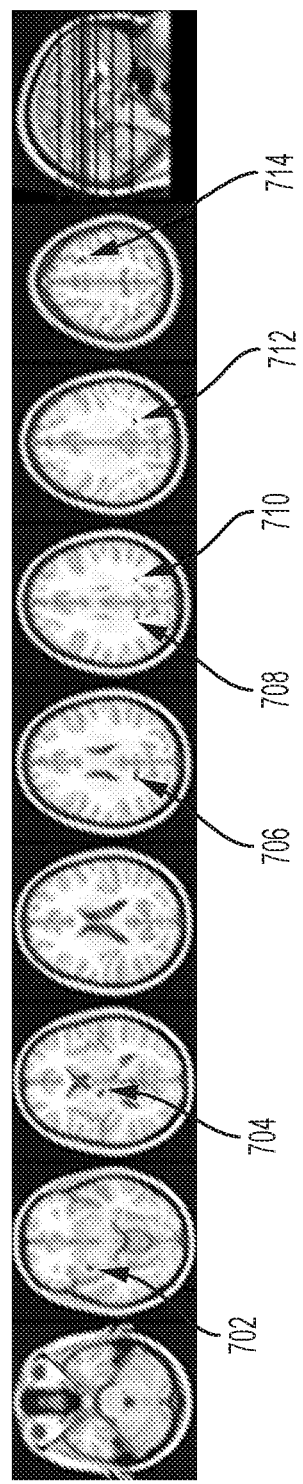
FIG. 7 illustrates DT-MRI whole voxel analysis of MD of an mTBI patient with a CUD>2SD compared to mTBI patients with CUD<2SD.

FIG. 7 illustrates DT-MRI whole voxel analysis of MD of an mTBI patient with a CUD>2SD compared to mTBI patients with CUD<2SD. Voxels with MD that significantly differed from uninjured control are indicated as 702, 704, 706, 708, 710, 712, and 714. This patient had 0.116% (126/108423) aberrant voxels. Patients with a CUD>2SD had voxels that significantly clustered in the left external capsule, left and right parietal, and right frontal lobes (p<0.01).

Whole voxel analysis of MD in injured patients significantly differed than controls (p<0.01) (FIG. 6). Whole voxel analysis was then repeated after separating the injured patients based upon the standard deviation of the CUD score. Whole voxel MD in patients with CUD z-scores>2 standard deviations differed significantly from patients with CUD values<2 standard deviations. MD differences tended to cluster in the left external capsule, left and right parietal and right frontal lobes. Patients with a CUD with a standard deviation>2 also differed significantly from uninjured controls (p<0.01) (FIG. 7). These data strongly suggest that this cohort of mTBI patients had a diffuse white matter injury despite some clustering FA and MD differences in specific white matter tracts. As a group, these changes became larger and more pronounced when patients were stratified based upon CUD standard deviation.

FA and MD were also examined in a region of interest analysis of twenty brain regions in the control, acute mTBI and rescan mTBI groups, as shown in Table 3, below:

TABLE 3

FA and MD in white matter regions of interest in control subjects and mTBI patients. The mTBI patients were scanned within one week of injury (acutely) and 6 months after injury (rescan). No significant differences were observed.

| Brain region | Control FA | Acute mTBI FA | Control MD (×10−4) | Acute mTBI MD (×10−4) | Rescan mTBI FA | Rescan mTBI MD (×10−4) |
|---|---|---|---|---|---|---|
| Anterior Corpus Callosum | 0.635 ± 0.016 | 0.643 ± 0.015 | 8.616 ± 0.182 | 8.668 ± 0.201 | 0.634 ± 0.022 | 8.667 ± 0.004 |
| Posterior Corpus Callosum | 0.709 ± 0.017 | 0.719 ± 0.012 | 8.191 ± 0.124 | 8.113 ± 0.160 | 0.707 ± 0.018 | 8.29 ± 0.17 |
| Cingulum left | 0.507 ± 0.009 | 0.514 ± 0.11 | 6.627 ± 0.008 | 6.693 ± 0.008 | 0.509 ± 0.015 | 6.69 ± 0.007 |
| Cingulum right | 0.490 ± 0.012 | 0.493 ± 0.012 | 6.589 ± 0.007 | 6.654 ± 0.007 | 0.475 ± 0.017 | 6.69 ± 0.008 |
| Forceps Major | 0.568 ± 0.008 | 0.568 ± 0.008 | 7.188 ± 0.004 | 7.185 ± 0.004 | 0.567 ± 0.008 | 7.34 ± 0.005 |
| Forceps Minor | 0.506 ± 0.010 | 0.513 ± 0.007 | 7.237 ± 0.009 | 7.255 ± 0.007 | 0.499 ± 0.008 | 7.36 ± 0.010 |
| Cortical-spinal left | 0.663 ± 0.008 | 0.654 ± 0.007 | 6.430 ± 0.005 | 6.440 ± 0.005 | 0.653 ± 0.008 | 6.49 ± 0.006 |
| Cortical-spinal right | 0.648 ± 0.008 | 0.640 ± 0.007 | 6.485 ± 0.007 | 6.592 ± 0.005 | 0.646 ± 0.008 | 6.60 ± 0.005 |
| Frontal aslant Path left | 0.463 ± 0.009 | 0.464 ± 0.005 | 6.616 ± 0.005 | 6.632 ± 0.006 | 0.474 ± 0.008 | 6.67 ± 0.004 |
| Frontal aslant Path right | 0.459 ± 0.009 | 0.452 ± 0.005 | 6.686 ± 0.006 | 6.774 ± 0.006 | 0.455 ± 0.009 | 6.81 ± 0.006 |
| Fronto-occipital fasciculus left | 0.538 ± 0.008 | 0.537 ± 0.007 | 7.108 ± 0.007 | 7.121 ± 0.007 | 0.543 ± 0.005 | 7.13 ± 0.010 |
| Fronto-occipital fasciculus right | 0.498 ± 0.009 | 0.494 ± 0.007 | 7.042 ± 0.009 | 7.107 ± 0.006 | 0.492 ± 0.006 | 7.17 ± 0.003 |
| Inferior longitudinal fasciculus Left | 0.517 ± 0.007 | 0.513 ± 0.007 | 6.966 ± 0.008 | 6.970 ± 0.008 | 0.517 ± 0.006 | 7.01 ± 0.012 |
| Inferior longitudinal fasciculus Right | 0.521 ± 0.010 | 0.514 ± 0.008 | 6.821 ± 0.009 | 6.899 ± 0.12 | 0.517 ± 0.009 | 6.96 ± 0.004 |
| Superior longitudinal fasciculus Left | 0.522 ± 0.010 | 0.524 ± 0.007 | 6.678 ± 0.004 | 6.736 ± 0.008 | 0.527 ± 0.011 | 6.76 ± 0.006 |
| Superior longitudinal fasciculus Right | 0.524 ± 0.013 | 0.519 ± 0.011 | 6.873 ± 0.008 | 6.934 ± 0.005 | 0.520 ± 0.023 | 7.00 ± 0.003 |
| Perforant Path Left | 0.467 ± 0.010 | 0.461 ± 0.012 | 7.101 ± 0.009 | 6.980 ± 0.010 | 0.469 ± 0.011 | 6.84 ± 0.15 |
| Perforant Path Right | 0.487 ± 0.011 | 0.482 ± 0.010 | 6.570 ± 0.007 | 6.566 ± 0.007 | 0.493 ± 0.015 | 6.54 ± 0.013 |
| UF left | 0.447 ± 0.006 | 0.439 ± 0.008 | 6.990 ± 0.004 | 7.047 ± 0.006 | 0.436 ± 0.011 | 7.08 ± 0.009 |
| UF Right | 0.467 ± 0.009 | 0.465 ± 0.009 | 7.027 ± 0.007 | 7.123 ± 0.006 | 0.453 ± 0.012 | 7.20 ± 0.013 |

Unlike the injured group, the control group was not rescanned since the FA and MD values do not to change over time. Tract-Based Spatial Statistics (TBSS) analysis used an atlas of tracts of interest to extract portions of the TBSS-derived skeleton that represent well-centered voxels in white matter tract. Groups were compared using mean values for the voxels in the tract. Controls (n=10) and injured (n=14) patients did not significantly differ in the following white matter tracts: Anterior corpus callosum; Posterior corpus callosum; Cingulum left and right; Corticospinal tract left and right; Frontal aslant tract left and right; Forceps Major; Forceps minor; Fronto-occipital fasciculus right and left; Inferior longitudinal fasciculus, left and right; Perforant path, left and right; Superior longitudinal fasciculus, left and right; Uncinate fasciculus, left and right (data not shown (data not shown). FA and MD were computed in the 20 tracts. FA and MD were compared between injured patients with a CUD<2 standard deviations with those with a CUD>2 standard deviations. MD in the posterior corpus callosum trended strongly toward significance (ANOVA, $F_{2,23}$=2.33, p=0.12, CUD<2 standard deviations vs CUD>2 standard deviations, p=0.058). No significant differences were seen in the rescan group.

In contrast, individual mTBI patients were analyzed by Spearman's correlations performed between multiple the CUD using the Benjamini-Hochberg correction. FIG. 10A illustrates a significant correlation between FA in the left corticospinal tract and CUD T-Scores. FA data were analyzed using TBSS and then compared to CUD T-Scores using Spearman's correlations. A false discovery rate using a Benjamini-Hochberg correction of 0.05 yielded a q=0.0113 of the FA data and the MD data in FIG. 10B. A significant correlation was found between the Fractional Anisotropy of the left corticospinal tract and the CUD (r=0.715, p=0.005).

FIG. 10B illustrates a significant correlation between MD in the posterior corpus callosum and CUD T-Scores. MD data were analyzed using tract-based special statistics and then compared to CUD T-Scores using Spearman's correlations. A false discovery rate using a Benjamini-Hochberg correction of 0.05 yielded a q=0.0113 of the FA data in FIG. 10A and the MD data. A significant correlation was found between the Mean Diffusivity of the posterior corpus callosum and the CUD (r=−0.811, p<0.001).

Figure 8:
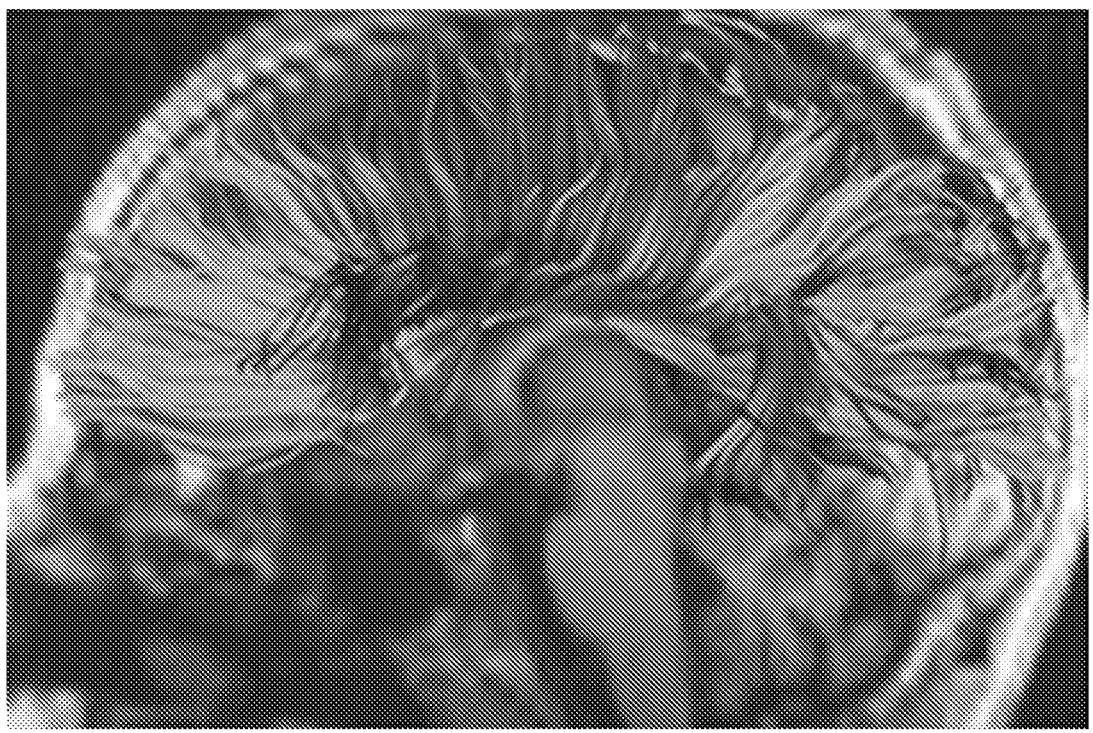
FIG. 8 illustrates tractography analysis of corpus callosum.

Tractography was performed on the corpus callosum since radiological abnormalities in corpus callosum may correlate with deficits in CUD. An example of corpus callosum tractography is shown in FIG. 8.

Figure 9A:
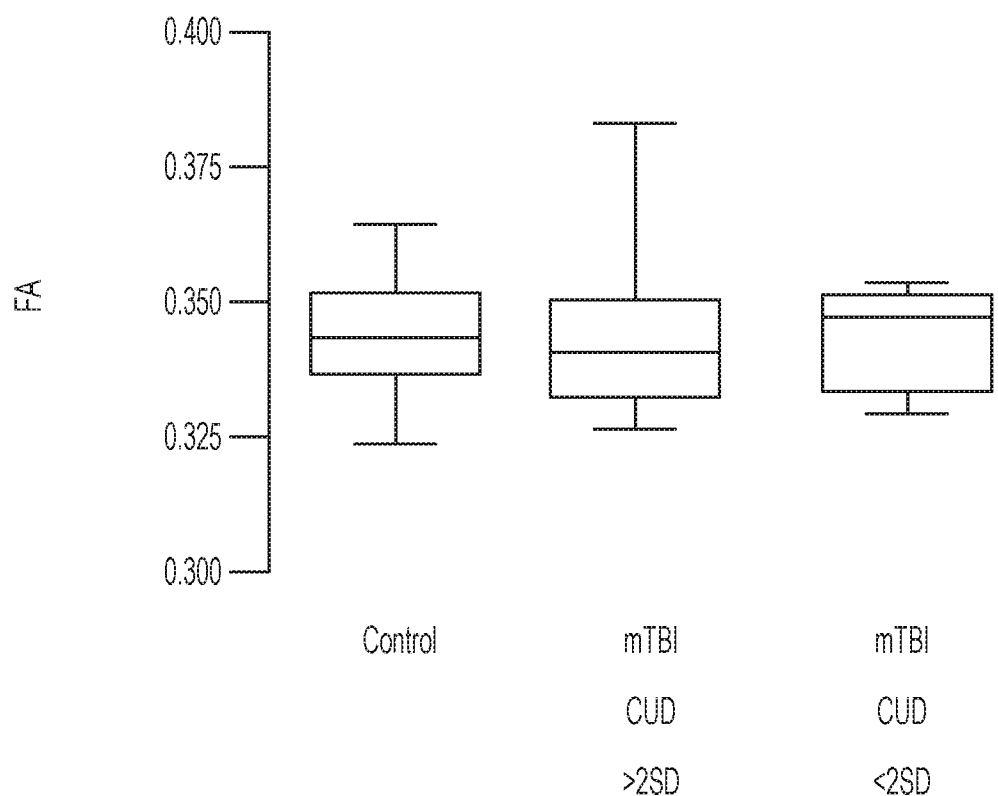
FIG. 9A illustrates FA in the corpus callosum.

FIG. 9A illustrates FA in the corpus callosum. There was no significant difference ("NS") in FA in control, mTBI patients with a CUD>2SD and mTBI patients with a CUD<2SD. Boxes show the 1st and 3rd quartile of the data; the line shows the median and the whiskers show the SD.

Figure 9B:
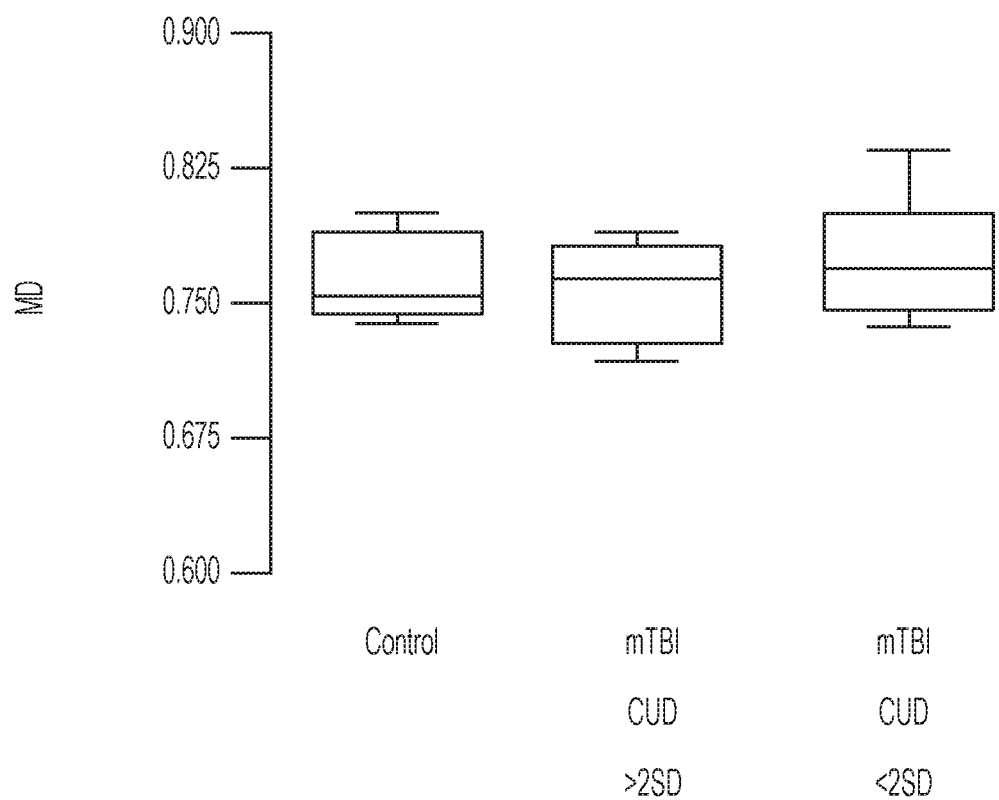
FIG. 9B illustrates Mean Diffusivity using tractography in the corpus callosum.

FIG. 9B illustrates Mean Diffusivity using tractography in the corpus callosum. There was no significant difference in MD in control, mTBI patients with a CUD>2SD and mTBI patients with a CUD<2SD. Boxes show the 1st and 3rd quartile of the data; the line shows the median and the whiskers show the SD.

Twelve injured patients and nine controls received the battery of neuropsychological tests that included Digit Symbol, Symbol Search, Digit Span, Controlled Oral Word Test, Trails A and B, Brief Symptom Inventory and California Verbal Learning Test, as shown in Table 4, below:

TABLE 4

Controls and mTBI patients performed similarly on Brief Symptom Inventory subtests of Somatization, Depression, Interpersonal Sensitivity, Obsessive Compulsive, Hostility, Anxiety, Phobia, Paranoia, or Pychoticism. Positive Symptoms Total, Positive Symptoms Distress Index (data not shown).

| Test | Controls | mTBI | t test comparison of controls and mTBI | CUD score < 2 SD | CUD score > 2SD | Post-hoc ANOVA statistic comparing CUD score < 2 SD vs. >2 SD |
|---|---|---|---|---|---|---|
| Processing speed index | 108 ± 4.0 | 88.4 ± 3.2 | $t_{16}$ = 3.7 p < 0.002 | 85.3 ± 0.7 | 90.2 ± 5.1 | NS |
| Digit Symbol | 11.3 ± 0.7 | 6.4 ± 0.5 | NS | 6.8 ± 0.7 | 5.7 ± 0.3 | NS |
| Digit Span | 11.0 ± 0.6 | 7.9 ± 0.9 | $t_{16}$ = 3.4 p < 0.005 | 9.0 ± 0.9 | 6.0 ± 1.0 | NS |
| COWAT | 50 ± 2.8 | 26.6 ± 5.5 | $t_{16}$ = 2.3 p < 0.05 | 13.3 ± 6.3 | 34.6 ± 5.3 | $F_{2, 16}$ = 15.95, p < 0.001; p < 0.02 |
| Trail Marking Test A | 50.2 ± 3.0 | 41.9 ± 3.7 | NS | 37.7 ± 5.7 | 44.4 ± 4.9 | NS |
| Trail Marking Test B | 46.8 ± 6.6 | 94.0 ± 15.0 | NS | 85.6 ± 21.4 | 108.0 ± 20.0 | NS |
| Stroop 1 | 38.6 ± 1.6 | 55.9 ± 7.9 | $t_{15}$ = −2.3 p < 0.05 | 43.8 ± 4.4 | 76.0 ± 14.0 | $F_{2, 16}$ = 11.62 p < 0.0001; p < 0.002 |
| Stroop 2 | 83.2 ± 6.1 | 125.5 ± 17.1 | $t_{15}$ = −2.4 p < 0.05 | 110.0 ± 20.8 | 151.3 ± 27.7 | NS |
| Basic Symptom Inventory- Obsessive Compulsive | 60.6 ± 1.8 | 54.0 ± 6.1 | NS | 65.8 ± 6.1 | 38.3 ± 0.3 | $F_{2, 15}$ = 17.96 p < 0.001; p < 0.001 |
| Basic Symptom Inventory- Positive Symptoms Total | 54.6 ± 2.2 | 51.1 ± 5.8 | NS | 39.0 ± 9.0 | 60.3 ± 3.6 | $F_{2, 15}$ = 5.47 p < 0.02; p < 0.02 |

TABLE 4-continued

Controls and mTBI patients performed similarly on Brief Symptom Inventory subtests of Somatization, Depression, Interpersonal Sensitivity, Obsessive Compulsive, Hostility, Anxiety, Phobia, Paranoia, or Pychoticism. Positive Symptoms Total, Positive Symptoms Distress Index (data not shown).

| Test | Controls | mTBI | t test comparison of controls and mTBI | CUD score < 2 SD | CUD score > 2SD | Post-hoc ANOVA statistic comparing CUD score < 2 SD vs. >2 SD |
|---|---|---|---|---|---|---|
| Basic Symptom Inventory- Positive Symptoms Distress Index | 51.8 ± 1.5 | 53.3 ± 3.0 | NS | 56.0 ± 2.0 | 49.7 ± 6.7 | NS |
| Basic Symptom Inventory- Global Severity Index | 54.2 ± 2.3 | 52.9 ± 5.5 | NS | 60.8 ± 3.6 | 42.3 ± 9.3 | NS |
| California Verbal Learning Test Total Learning Slope, Trials 1-5 | 0.4 ± 0.2 | −0.9 ± 0.5 | $t_{14} = 3.1$ p 0.01 | 0.63 ± 0.3 | −1.3 ± 0.7 | NS |

Mild TBI patients were impaired when compared to controls in most of the timed tests that examined processing speed (processing speed index and the forward and backward components of the digit span, Stroop 1 and 2, Trails A and B and Controlled Oral Word Association Test ("COWAT"). They were also impaired on the California Verbal Learning Test, a test a verbal memory. In most of these tests mTBI patients with a CUD of <2 SD were no different than those with a CUD>2 SD (Table 4).

The Stroop 1 test and the COWAT revealed differences between patients with CUD scores<2 SD or >2 SD. In Stroop 1, subjects identify the names of colors that are in the same hue as the name. Stroop 1 prepared patients for the more cognitively challenging word-color interference in the Stroop 2 test. Mild TBI patients were impaired in both phases of the Stroop test. While the performance of patients with a CUD of >2 SD on Stroop 1 differed significantly from patients with a CUD of <2 SD, this difference was no longer present in the cognitively more difficult Stroop 2 test (Table 4). Previous studies did not report differences among mTBI patients on the Stroop 1 test.

The phonemic version of the COWAT test requires the patient to say as many words as possible starting with a single letter in a defined period of time. All TBI patients were impaired in this test, but those with a CUD>2 SD were more impaired than those with a CUD<2 SD (Table 4). Mild TBI patients were also impaired in the combined score of the Controlled Oral Word Association Test when compared to controls. Patients with a CUD>2 SD on the Controlled Oral Word Association Test differed significantly from patients with a CUD of <2 SD (Table 4).

The Obsessive-Compulsive subtest in the Basic Symptoms Inventory is widely believed to measuring features that go beyond obsessive-compulsive. This was first noted by Slaughter, et al., who noted that brain injured patients differ more than controls on the Obsessive-Compulsive subtest than any other subtest in the Basic Symptoms Inventory. The six items on the subtest are:
1) trouble remembering things
2) feeling blocked in getting things done
3) difficulty making decisions
4) your mind going blank
5) trouble concentrating
6) needing to repeatedly check what you do Controls and mTBI patients did not differ on the Obsessive-Compulsive subtest (Table 4). Mild TBI patients with a CUD>2 SD did differ from those with a CUD<2 SD suggesting more difficulty with the six items on the subtest (Table 4). Mild TBI patients were also impaired compared to controls on Trails A, the and the California Verbal Learning Test. Injured patients with CUD scores greater or less than 2 SD did not significantly differ on these tests (Table 4).

No differences were observed mTBI patients and controls on all subtests of the Brief Symptom Inventory (Table 4). Patients with a CUD>2SD differed significantly from controls in the anxiety and obsessive-compulsive components of the test. Patients with a CUD>2SD had more overall positive symptoms than controls. Patients with a CUD>2SD on the obsessive-compulsive components portions of the test differed significantly from patients with a CUD of <2SD. They also trended strongly (p=0.06) on the number of overall positive symptoms.

Some Observations

The IHT test finds deficits within 24 hours after injury (>2 SD) in either CRT, URT and CUD in 72.7% of mTBI patients. Deficits in URT were seen in 68.2% of injured patients; 45.5% had deficits in CRT. CUD deficits were seen in 40.9% of the patients.

Injured patients showed no difference in whole voxel analysis of FA. MD had a significant difference between injured and control. Post-hoc stratification of the injured patients based upon <2 SD or >2 SD revealed a population that significantly differed than controls in both whole voxel FA and MD. These data suggest that impairments in CUD correlate with increased radiological abnormalities on DT-MRI. This is further supported by the finding of highly significant correlations between the CUD and FA of the left corticospinal tract and the MD of the posterior corpus callosum.

The increased number of aberrant voxels in mTBI patients seen in whole voxel analysis could not be strongly localized to a specific white matter tract region of interest analysis as seen using tract-based spatial statistics or corpus callosum tractography. These support a model of mTBI producing a diffuse white matter damage.

mTBI and control patients differed on the forward and backward components of the digit span, Stroop 1 and 2, Trails A and B, COWAT and California Verbal Learning Test. On digit span, Trails A and B, and the California Verbal Learning Test, there was no difference in the performance on mTBI patients with CUD<2 SD and >2 SD.

mTBI patients with CUD<2 SD and >2 SD differed significantly on Stroop 1, COWAT and the anxiety and obsessive-compulsive components of the Basic Symptom Inventory.

Vision testing for Peripheral Reaction Time ("PRT") and CUD is easy, objective and non-invasive. The tests were completed within minutes using a laptop computer that reduces issues of fatigue or non-compliance. Patients could be stratified based upon CUD z-scores with a standard deviation of less or greater than 2. Patients with CUD having a standard deviation greater than 2 had significantly more white matter damage as seen in whole voxel analysis of FA and MD. Patients with CUD having a standard deviation greater than 2 performed significantly worse on a variety of neuropsychological tests: Stroop 1, COWAT and the anxiety and obsessive-compulsive components of the Basic Symptom Inventory. These data suggest that testing for PRT and CUD identifies patients with more damaging mTBI.

The tasks of the subject technology can be distinguished in at least some aspects from a multiple choice compatible task. In two-choice tasks, participants respond to one of two squares that appeared a distance on both sides of the central fixation point. A compatible response involved pressing a key with a hand on the same side as the stimulus (i.e., right peripheral field stimuli or left peripheral field stimuli). An incompatible response involved making a response with the index finger of the hand on the side opposite to that of the stimulus. In four-choice tasks, participants were required to respond to one of four squares, with two on each side of the fixation point. The compatible four-choice task required participants to respond, using the index (inner square) or middle (outer square) finger of the hand on the same side as the stimulus. For the incompatible task, participants were required to use the same finger as for the compatible task but with the hand on the side opposite to that of the stimulus.

Both the tasks of the subject technology and multiple choice compatible tasks use reaction times to visual stimuli to assess oculomotor function in patients with mild traumatic brain injury. Despite its apparent simplicity, control of eye movements by the brain are quite complex because they are controlled by many brain regions (the lateral intraparietal area, the frontal eye fields, the supplementary eye fields and the dorsolateral prefrontal cortex, the basal ganglia, superior colliculus, the reticular formation and the oculomotor vermis and the fastigial oculomotor regions of the cerebellum). Due to the fact that many brain regions must coordinate their activity, eye movement impairments are common in TBI. Sophisticated eye trackers can track eye actions directly to precisely measure eye movements. Alternatively, reaction times can be measured as an indirect measure of oculomotor function.

Both the tasks of the subject technology and multiple choice compatible tasks appear similar, yet result in very different outcomes. The large differences in outcomes suggest that the tests are measuring different aspects of brain function that control eye movements. Both the tasks of the subject technology and multiple choice compatible tasks enroll a similar cohort of patients with mild traumatic brain injury.

In one study, a 2-choice compatible task was applied. Uninjured control subjects had an average 2-choice compatible reaction time of 322±66 msec. Injured patients taking 2-choice compatible task had an average reaction time of 378±82 msec (56 msec slower than controls).

Uninjured control subjects had an average URT of 293±15 msecs, as determined by tests of the subject technology. Average URT reaction was 477±53 msecs (184 msec slower than controls).

The relative difficulties of the two tasks to control subjects are quite similar since the uninjured control reaction times measured by the two tests differ by only 9%. Yet, the URT reaction time deficit is 3.3 times larger than the equivalent deficit of the 2-choice compatible task. This data strongly suggests that the two tests are measuring different deficits in brain function since the similar reaction times in control patients are not seen with the mildly injured patients.

An even larger distinction between the two tests can be seen in a subset of 4 mildly injured patients in the URT as shown in FIG. 2. These patients had an average URT, reaction time of 933±81 msec resulting in a very large deficit of 688 msec. This deficit is 12.3 fold larger than the average deficit in the 2-choice compatible task. Deficits of this magnitude were not reported in the 2-choice compatible test.

This comparison suggests that, even though both tests use reaction times to indirectly measure eye movements, the peripheral reaction time test assesses a very different deficit. A key difference may be the distance traveled by the eye in the two studies. Mathias, et al., concludes that increasing the difficulty of the test yields more useful differences between control and mildly injured subjects. We, in fact, came to the opposite conclusion, that simplifying the test reveals more significant differences between the control and injured groups.

Systems

Figure 11:
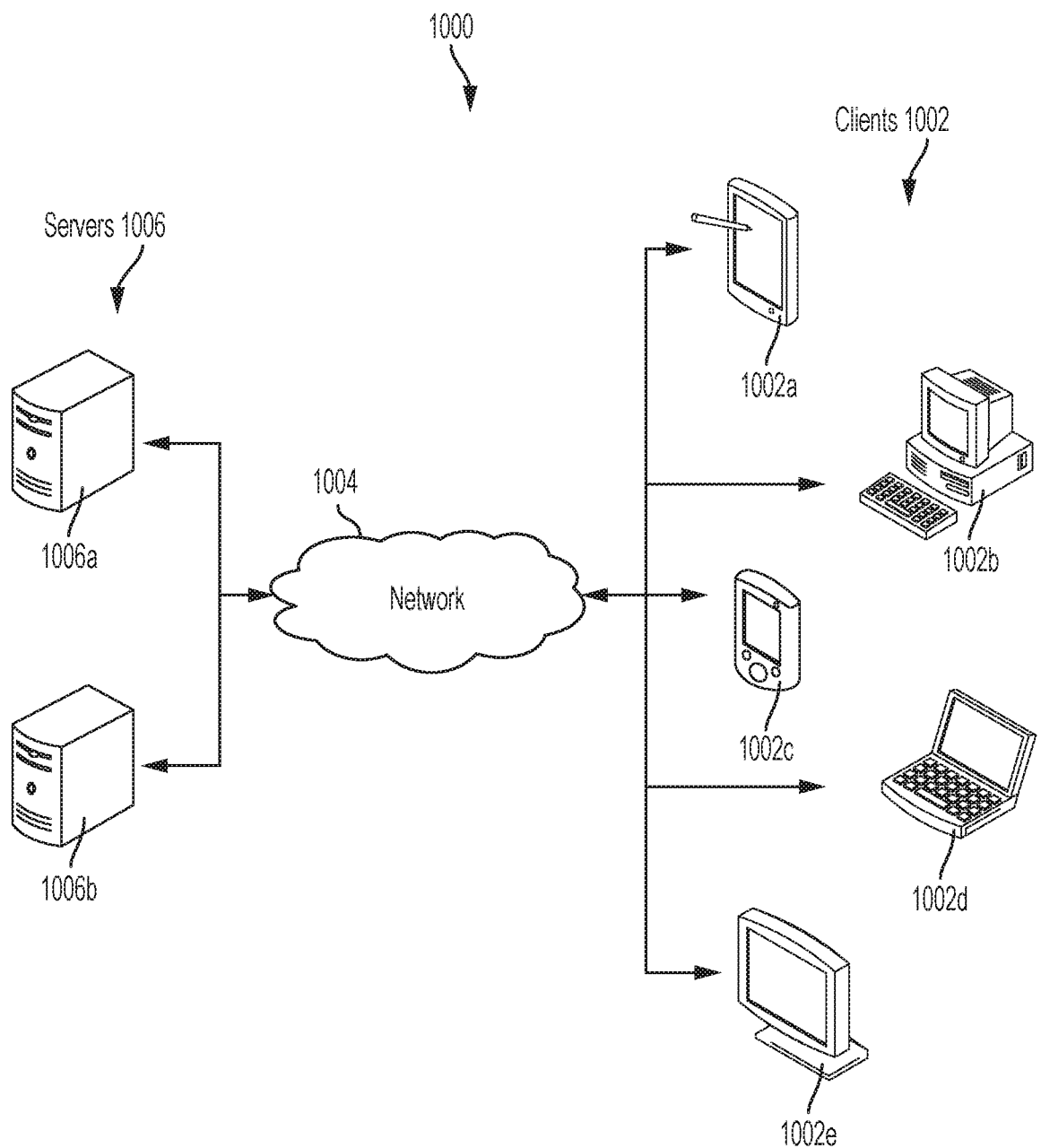
FIG. 11 is an exemplary diagram of a network in which systems and methods herein may be implemented.

FIG. 11 is a simplified diagram of a system 1000, in accordance with various embodiments of the subject technology. The system 1000 may include one or more remote client devices 1002 (e.g., client devices 1002a, 1002b, 1002c, 1002d, and 1002e) in communication with one or more server computing devices 1006 (e.g., servers 1006a and 1006b) via network 1004. In some embodiments, a client device 1002 is configured to run one or more applications based on communications with a server 1006 over a network 1004. In some embodiments, a server 1006 is configured to run one or more applications based on communications with a client device 1002 over the network 1004. In some embodiments, a server 1006 is configured to run one or more applications that may be accessed and controlled at a client device 1002. For example, a user at a client device 1002 may use a web browser to access and control an application running on a server 1006 over the network 1004. In some embodiments, a server 1006 is configured to allow remote sessions (e.g., remote desktop sessions) wherein users can access applications and files on a server 1006 by logging onto a server 1006 from a client device 1002. Such a connection may be established using any of several well-known techniques such as the Remote Desktop Protocol (RDP) on a Windows-based server.

By way of illustration and not limitation, in some embodiments, stated from a perspective of a server side (treating a server as a local device and treating a client device as a remote device), a server application is executed (or runs) at a server 1006. While a remote client device 1002 may receive and display a view of the server application on a display local to the remote client device 1002, the remote client device 1002 does not execute (or run) the server application at the remote client device 1002. Stated in another way from a perspective of the client side (treating a server as remote device and treating a client device as a local device), a remote application is executed (or runs) at a remote server 1006.

By way of illustration and not limitation, in some embodiments, a client device 1002 can represent a desktop computer, a mobile phone, a laptop computer, a netbook computer, a tablet, a thin client device, a personal digital assistant (PDA), a portable computing device, and/or a suitable device with a processor. In one example, a client device 1002 is a smartphone (e.g., iPhone, Android phone, Blackberry, etc.). In certain configurations, a client device 1002 can represent an audio player, a game console, a camera, a camcorder, a Global Positioning System (GPS) receiver, a television set top box an audio device, a video device, a multimedia device, and/or a device capable of supporting a connection to a remote server. In some embodiments, a client device 1002 can be mobile. In some embodiments, a client device 1002 can be stationary. According to certain embodiments, a client device 1002 may be a device having at least a processor and memory, where the total amount of memory of the client device 1002 could be less than the total amount of memory in a server 1006. In some embodiments, a client device 1002 does not have a hard disk. In some embodiments, a client device 1002 has a display smaller than a display supported by a server 1006. In some aspects, a client device 1002 may include one or more client devices.

In some embodiments, a server 1006 may represent a computer, a laptop computer, a computing device, a virtual machine (e.g., VMware® Virtual Machine), a desktop session (e.g., Microsoft Terminal Server), a published application (e.g., Microsoft Terminal Server), and/or a suitable device with a processor. In some embodiments, a server 1006 can be stationary. In some embodiments, a server 1006 can be mobile. In certain configurations, a server 1006 may be any device that can represent a client device. In some embodiments, a server 1006 may include one or more servers.

In some embodiments, a first device is remote to a second device when the first device is not directly connected to the second device. In some embodiments, a first remote device may be connected to a second device over a communication network such as a Local Area Network (LAN), a Wide Area Network (WAN), and/or other network.

When a client device 1002 and a server 1006 are remote with respect to each other, a client device 1002 may connect to a server 1006 over the network 1004, for example, via a modem connection, a LAN connection including the Ethernet or a broadband WAN connection including DSL, Cable, T1, T3, Fiber Optics, Wi-Fi, and/or a mobile network connection including GSM, GPRS, 3G, 4G, 4G LTE, WiMax or other network connection. Network 1004 can be a LAN network, a WAN network, a wireless network, the Internet, an intranet, and/or other network. The network 1004 may include one or more routers for routing data between client devices and/or servers. A remote device (e.g., client device, server) on a network may be addressed by a corresponding network address, such as, but not limited to, an Internet protocol (IP) address, an Internet name, a Windows Internet name service (WINS) name, a domain name, and/or other system name. These illustrate some examples as to how one device may be remote to another device, but the subject technology is not limited to these examples.

According to certain embodiments of the subject technology, the terms "server" and "remote server" are generally used synonymously in relation to a client device, and the word "remote" may indicate that a server is in communication with other device(s), for example, over a network connection(s).

According to certain embodiments of the subject technology, the terms "client device" and "remote client device" are generally used synonymously in relation to a server, and the word "remote" may indicate that a client device is in communication with a server(s), for example, over a network connection(s).

In some embodiments, a "client device" may be sometimes referred to as a client or vice versa. Similarly, a "server" may be sometimes referred to as a server device or server computer or like terms.

In some embodiments, the terms "local" and "remote" are relative terms, and a client device may be referred to as a local client device or a remote client device, depending on whether a client device is described from a client side or from a server side, respectively. Similarly, a server may be referred to as a local server or a remote server, depending on whether a server is described from a server side or from a client side, respectively. Furthermore, an application running on a server may be referred to as a local application, if described from a server side, and may be referred to as a remote application, if described from a client side.

In some embodiments, devices placed on a client side (e.g., devices connected directly to a client device(s) or to one another using wires or wirelessly) may be referred to as local devices with respect to a client device and remote devices with respect to a server. Similarly, devices placed on a server side (e.g., devices connected directly to a server(s) or to one another using wires or wirelessly) may be referred to as local devices with respect to a server and remote devices with respect to a client device.

Figure 12:
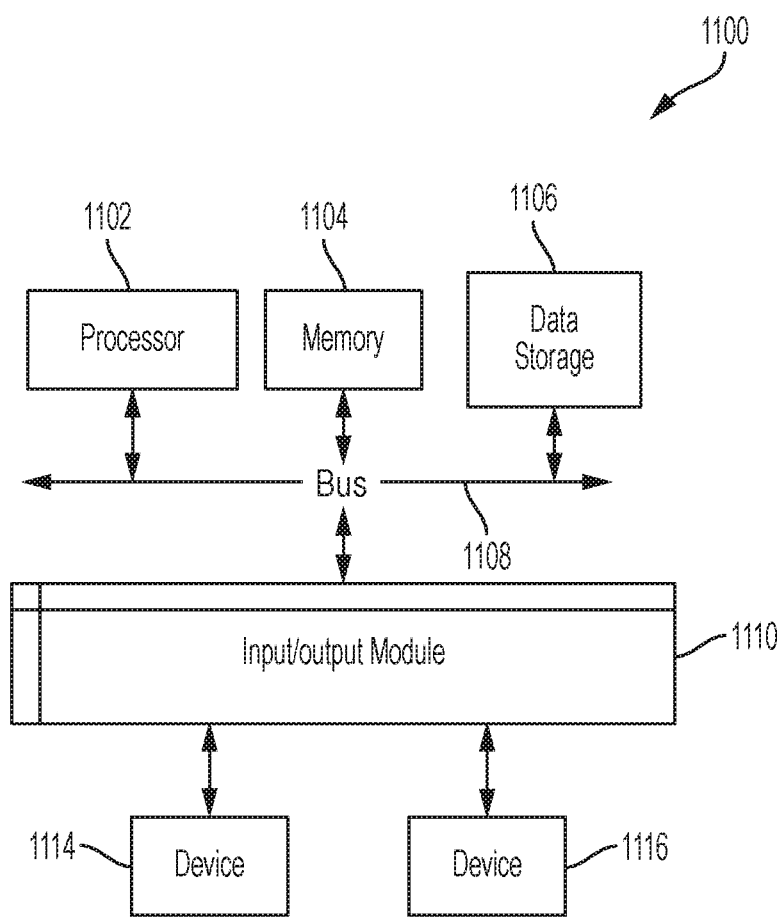
FIG. 12 is an exemplary diagram of a client or server of FIG. 10.
Figure 13:
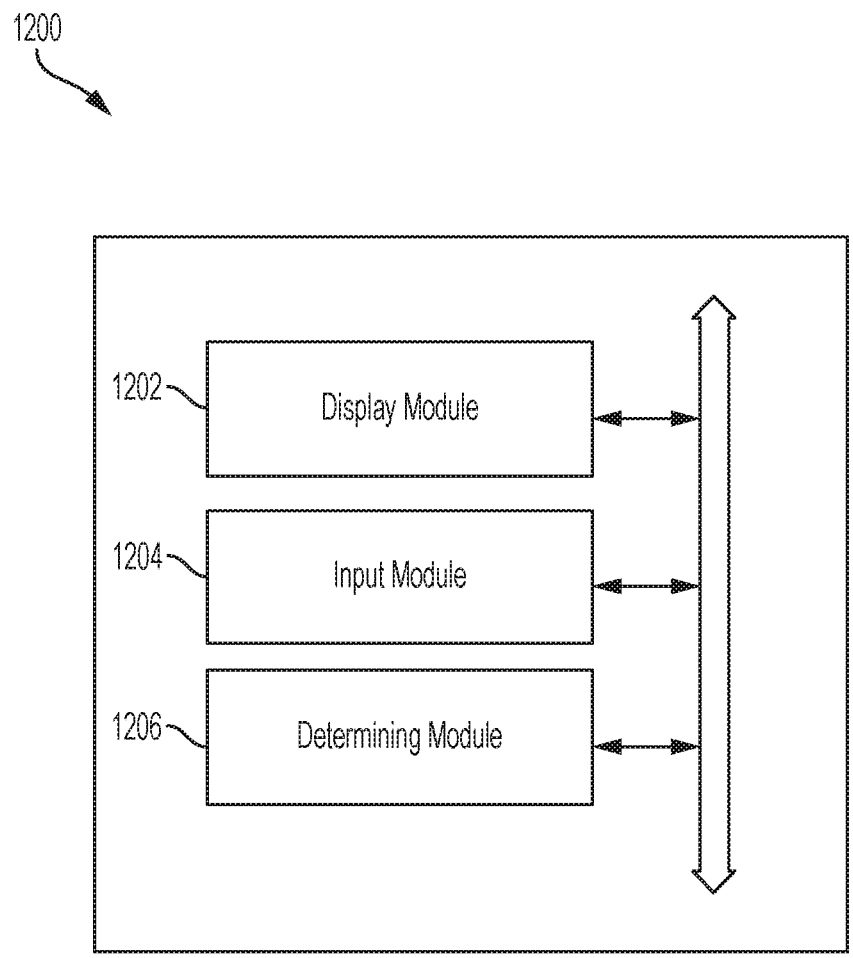
FIG. 13 is an exemplary diagram of modules implementing methods of the subject technology.

FIG. 12 is a block diagram illustrating an exemplary computer system 1100 with which a client device 1002 and/or a server 1006 of FIG. 11 can be implemented. In certain embodiments, the computer system 1100 may be implemented using hardware or a combination of software and hardware, either in a dedicated server, or integrated into another entity, or distributed across multiple entities.

The computer system 1100 (e.g., client 1002 and servers 1006) includes a bus 1108 or other communication mechanism for communicating information, and a processor 1102 coupled with the bus 1108 for processing information. By way of example, the computer system 1100 may be implemented with one or more processors 1102. The processor 1102 may be a general-purpose microprocessor, a microcontroller, a Digital Signal Processor (DSP), an Application Specific Integrated Circuit (ASIC), a Field Programmable Gate Array (FPGA), a Programmable Logic Device (PLD), a controller, a state machine, gated logic, discrete hardware components, and/or any other suitable entity that can perform calculations or other manipulations of information.

The computer system 1100 can include, in addition to hardware, code that creates an execution environment for the computer program in question, e.g., code that constitutes processor firmware, a protocol stack, a database management system, an operating system, or a combination of one or more of them stored in an included memory 1104, such as a Random Access Memory (RAM), a flash memory, a Read Only Memory (ROM), a Programmable Read-Only Memory (PROM), an Erasable PROM (EPROM), registers, a hard disk, a removable disk, a CD-ROM, a DVD, and/or any other suitable storage device, coupled to the bus 1108 for storing information and instructions to be executed by the processor 1102. The processor 1102 and the memory 1104 can be supplemented by, or incorporated in, special purpose logic circuitry.

The instructions may be stored in the memory 1104 and implemented in one or more computer program products, i.e., one or more modules of computer program instructions encoded on a computer readable medium for execution by, or to control the operation of, the computer system 1100, and according to any method well known to those of skill in the art, including, but not limited to, computer languages such as data-oriented languages (e.g., SQL, dBase), system languages (e.g., C, Objective-C, C++, Assembly), architectural languages (e.g., Java, .NET), and/or application languages (e.g., PHP, Ruby, Perl, Python). Instructions may also be implemented in computer languages such as array languages, aspect-oriented languages, assembly languages, authoring languages, command line interface languages, compiled languages, concurrent languages, curly-bracket languages, dataflow languages, data-structured languages, declarative languages, esoteric languages, extension languages, fourth-generation languages, functional languages, interactive mode languages, interpreted languages, iterative languages, list-based languages, little languages, logic-based languages, machine languages, macro languages, metaprogramming languages, multiparadigm languages, numerical analysis, non-English-based languages, object-oriented class-based languages, object-oriented prototype-based languages, off-side rule languages, procedural languages, reflective languages, rule-based languages, scripting languages, stack-based languages, synchronous languages, syntax handling languages, visual languages, wirth languages, and/or xml-based languages. The memory 1104 may also be used for storing temporary variable or other intermediate information during execution of instructions to be executed by the processor 1102.

A computer program as discussed herein does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, subprograms, or portions of code). A computer program can be deployed to be executed on one computer or on multiple computers that are located at one site or distributed across multiple sites and interconnected by a communication network. The processes and logic flows described in this specification can be performed by one or more programmable processors executing one or more computer programs to perform functions by operating on input data and generating output.

The computer system 1100 further includes a data storage device 1106 such as a magnetic disk or optical disk, coupled to the bus 1108 for storing information and instructions. The computer system 1100 may be coupled via an input/output module 1110 to various devices (e.g., devices 1114 and 1116). The input/output module 1110 can be any input/output module. Exemplary input/output modules 1110 include data ports (e.g., USB ports), audio ports, and/or video ports. In some embodiments, the input/output module 1110 includes a communications module. Exemplary communications modules include networking interface cards, such as Ethernet cards, modems, and routers. In certain aspects, the input/output module 1110 is configured to connect to a plurality of devices, such as an input device 1114 and/or an output device 1116. Exemplary input devices 1114 include a keyboard and/or a pointing device (e.g., a mouse or a trackball) by which a user can provide input to the computer system 1100. Other kinds of input devices 1114 can be used to provide for interaction with a user as well, such as a tactile input device, visual input device, audio input device, and/or brain-computer interface device. For example, feedback provided to the user can be any form of sensory feedback (e.g., visual feedback, auditory feedback, and/or tactile feedback), and input from the user can be received in any form, including acoustic, speech, tactile, and/or brain wave input. Exemplary output devices 1116 include display devices, such as a cathode ray tube (CRT) or liquid crystal display (LCD) monitor, for displaying information to the user.

According to certain embodiments, a client device 1002 and/or server 1006 can be implemented using the computer system 1100 in response to the processor 1102 executing one or more sequences of one or more instructions contained in the memory 1104. Such instructions may be read into the memory 1104 from another machine-readable medium, such as the data storage device 1106. Execution of the sequences of instructions contained in the memory 1104 causes the processor 1102 to perform the process steps described herein. One or more processors in a multi-processing arrangement may also be employed to execute the sequences of instructions contained in the memory 1104. In some embodiments, hard-wired circuitry may be used in place of or in combination with software instructions to implement various aspects of the present disclosure. Thus, aspects of the present disclosure are not limited to any specific combination of hardware circuitry and software.

Various aspects of the subject matter described in this specification can be implemented in a computing system that includes a back end component (e.g., a data server), or that includes a middleware component (e.g., an application server), or that includes a front end component (e.g., a client computer having a graphical user interface and/or a Web browser through which a user can interact with an implementation of the subject matter described in this specification), or any combination of one or more such back end, middleware, or front end components. The components of the system 1100 can be interconnected by any form or medium of digital data communication (e.g., a communication network). Examples of communication networks include a local area network and a wide area network.

The term "machine-readable storage medium" or "computer readable medium" as used herein refers to any medium or media that participates in providing instructions to the processor 1102 for execution. Such a medium may take many forms, including, but not limited to, non-volatile media, volatile media, and transmission media. Non-volatile media include, for example, optical or magnetic disks, such as the data storage device 1106. Volatile media include dynamic memory, such as the memory 1104. Transmission media include coaxial cables, copper wire, and fiber optics, including the wires that comprise the bus 1108. Common forms of machine-readable media include, for example, floppy disk, a flexible disk, hard disk, magnetic tape, any other magnetic medium, a CD-ROM, DVD, any other optical medium, punch cards, paper tape, any other physical medium with patterns of holes, a RAM, a PROM, an EPROM, a FLASH EPROM, any other memory chip or cartridge, or any other medium from which a computer can read. The machine-readable storage medium can be a machine-readable storage device, a machine-readable storage substrate, a memory device, a composition of matter effecting a machine-readable propagated signal, or a combination of one or more of them.

As used herein, a "processor" can include one or more processors, and a "module" can include one or more modules.

In an aspect of the subject technology, a machine-readable medium is a computer-readable medium encoded or stored with instructions and is a computing element, which defines structural and functional relationships between the instructions and the rest of the system, which permit the instructions' functionality to be realized. Instructions may be executable, for example, by a system or by a processor of the system. Instructions can be, for example, a computer program including code. A machine-readable medium may comprise one or more media.

FIG. 12 illustrates an example of a system 1200 for delivering sensory information to a subject mammal, in accordance with various embodiments of the subject technology. The system 1200 is an example of an implementation of a client device 1002 and/or a server 1006 for delivering sensory information to a subject mammal. The system 1200 comprises a display module 1202, an input module 1204, and/or a determining module 1206. Although the system 1200 is shown as having these modules, the system 1200 may have other suitable configurations. The modules of the system 1200 may be in communication with one another. In some embodiments, the modules may be implemented in software (e.g., subroutines and code). For example, the modules may be stored in the memory 1104 and/or data storage 1106, and executed by the processor 1102. In some aspects, some or all of the modules may be implemented in hardware (e.g., an Application Specific Integrated Circuit (ASIC), a Field Programmable Gate Array (FPGA), a Programmable Logic Device (PLD), a controller, a state machine, gated logic, discrete hardware components, or any other suitable devices) and/or a combination of both. Additional features and functions of these modules according to various aspects of the subject technology are further described in the present disclosure.

As used herein, the word "module" refers to logic embodied in hardware or firmware, or to a collection of software instructions, possibly having entry and exit points, written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors. The modules described herein are preferably implemented as software modules, but may be represented in hardware or firmware.

It is contemplated that the modules may be integrated into a fewer number of modules. One module may also be separated into multiple modules. The described modules may be implemented as hardware, software, firmware or any combination thereof. Additionally, the described modules may reside at different locations connected through a wired or wireless network, or the Internet.

In general, it will be appreciated that the processors can include, by way of example, computers, program logic, or other substrate configurations representing data and instructions, which operate as described herein. In other embodiments, the processors can include controller circuitry, processor circuitry, processors, general purpose single-chip or multi-chip microprocessors, digital signal processors, embedded microprocessors, microcontrollers and the like.

Furthermore, it will be appreciated that in one embodiment, the program logic may advantageously be implemented as one or more components. The components may advantageously be configured to execute on one or more processors. The components include, but are not limited to, software or hardware components, modules such as software modules, object-oriented software components, class components and task components, processes methods, functions, attributes, procedures, subroutines, segments of program code, drivers, firmware, microcode, circuitry, data, databases, data structures, tables, arrays, and variables.

Figure 14:
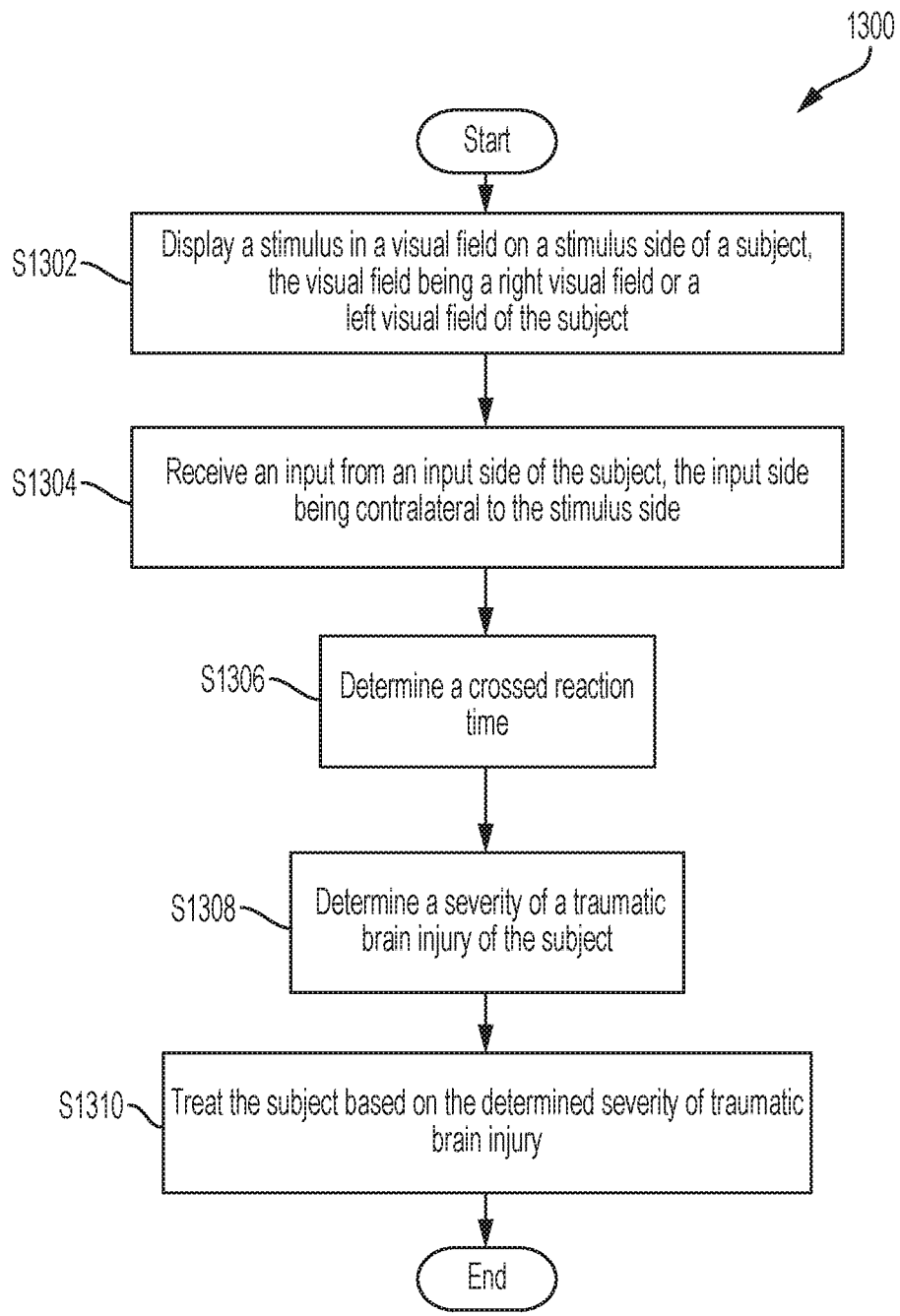
FIG. 14 is a flowchart of exemplary processing according to some methods and systems of the subject technology.
Figure 15:
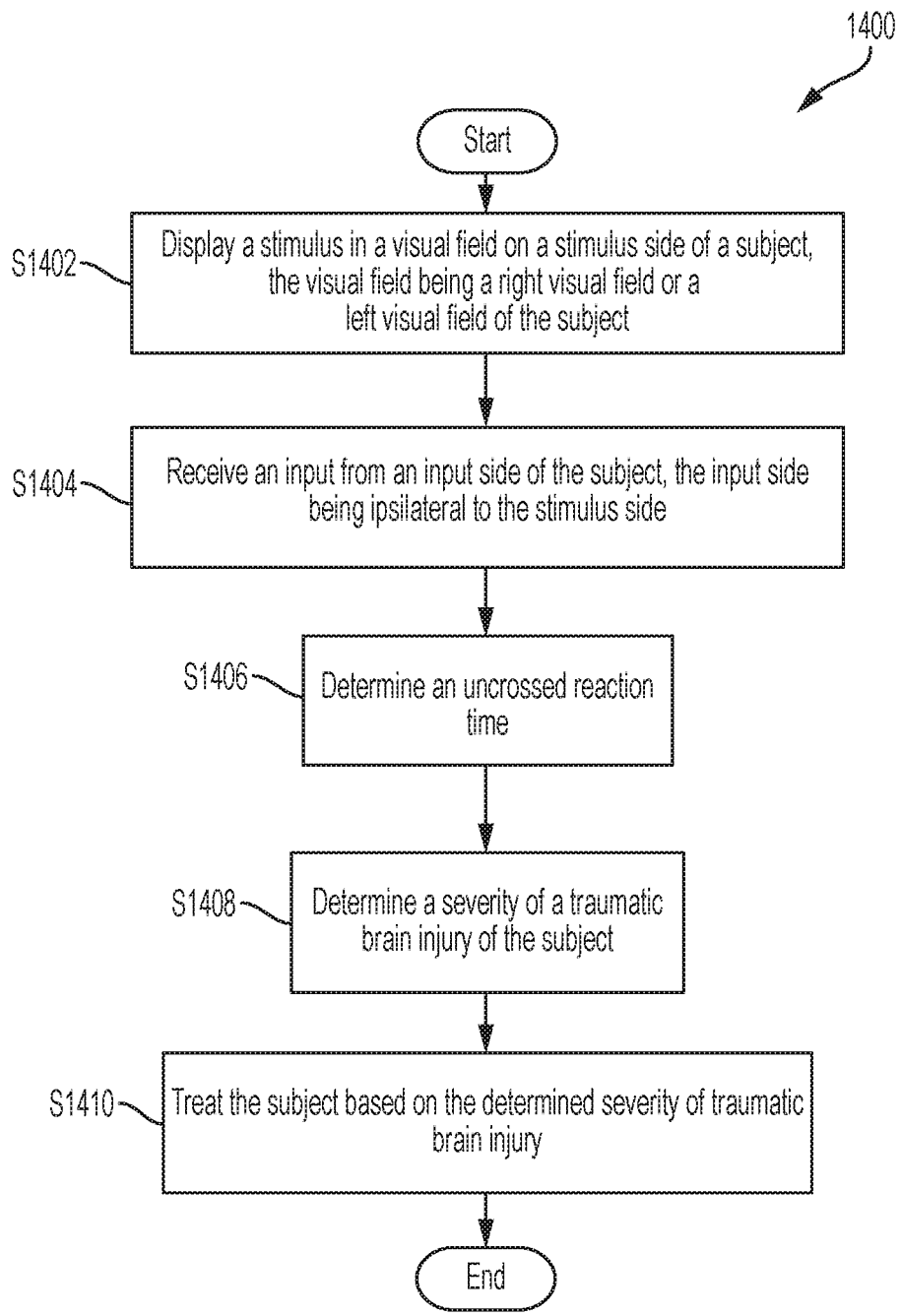
FIG. 15 is a flowchart of exemplary processing according to some methods and systems of the subject technology.
Figure 16:
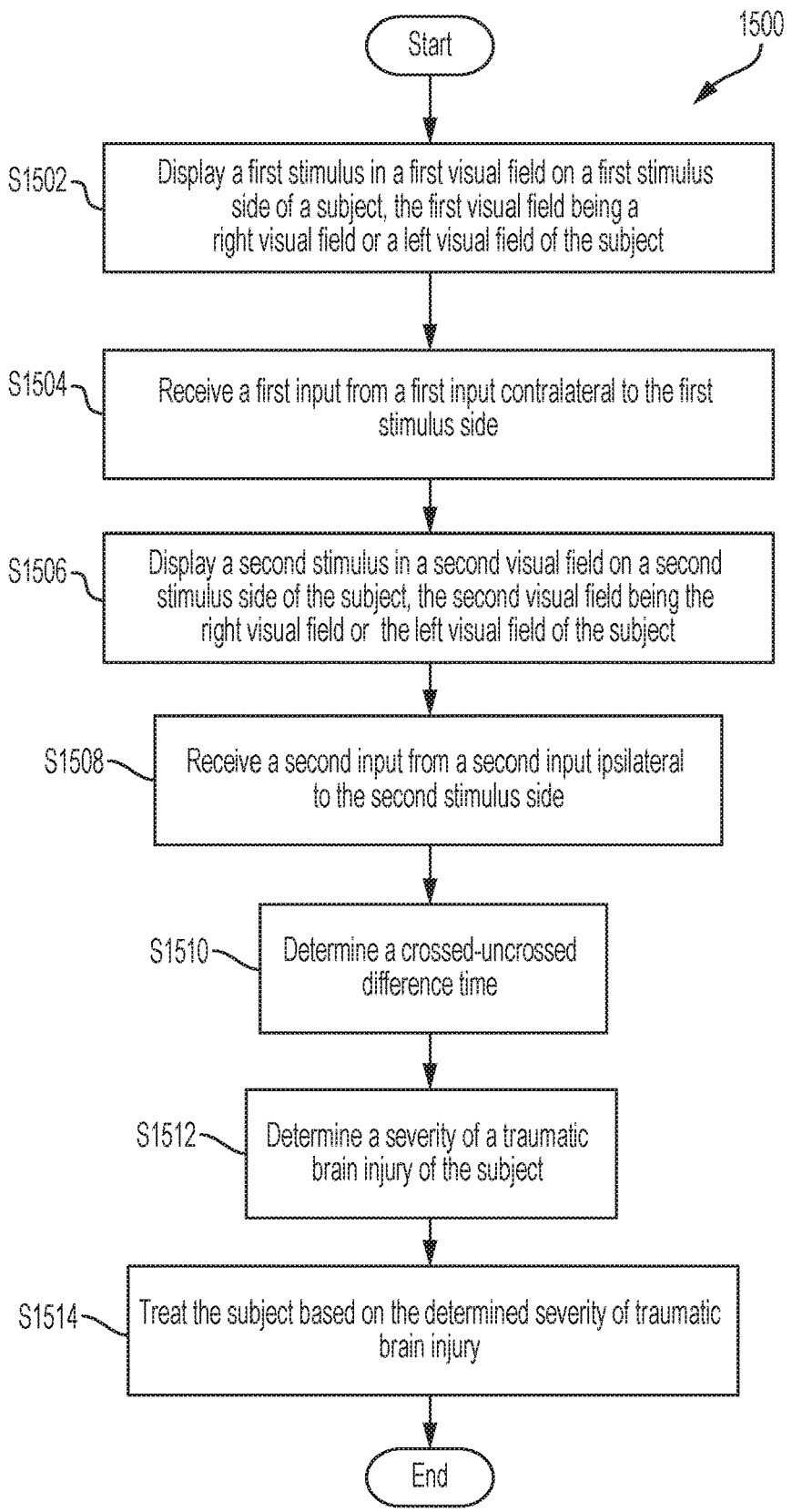
FIG. 16 is a flowchart of exemplary processing according to some methods and systems of the subject technology.

FIG. 14 illustrates an example of a method 1300 for determining a severity of a Traumatic Brain Injury, in accordance with various embodiments of the subject technology. The method 1300 is an example of an implementation of system 1200 for delivering sensory information to a subject mammal. The method 1300 comprises an operation s1302 to display a stimulus in a visual field on a stimulus side of a subject, the visual field being a right visual field or a left visual field of the subject. The method 1300 further comprises an operation s1304 to receive an input from an input side of the subject, the input side being contralateral to the stimulus side. The method 1300 further comprises an operation s1306 to determine a crossed reaction time comprising a span of time between displaying the stimulus and receiving the input. The method 1300 further comprises an operation s1308 to determine a severity of a Traumatic Brain Injury of the subject. The method 1300 further comprises an operation s1310 to treat the subject based on the determined severity of Traumatic Brain Injury FIG. 15 illustrates an example of a method 1400 for determining a severity of a Traumatic Brain Injury, in accordance with various embodiments of the subject technology. The method 1400 is an example of an implementation of system 1200 for delivering sensory information to a subject mammal. The method 1400 comprises an operation s1402 to display a stimulus in a visual field on a stimulus side of a subject, the visual field being a right visual field or a left visual field of the subject. The method 1400 further comprises an operation s1404 to receive an input from an input side of the subject, the input side being ipsilateral to the stimulus side. The method 1400 further comprises an operation s1406 to determine an uncrossed reaction time comprising a span of time between displaying the stimulus and receiving the input. The method 1400 further comprises an operation s1408 to determine a severity of a Traumatic Brain Injury of the subject. The method 1400 further comprises an operation s1410 to treat the subject based on the determined severity of Traumatic Brain Injury FIG. 16 illustrates an example of a method 1500 for delivering sensory information to a subject mammal, in accordance with various embodiments of the subject technology. The method 1500 is an example of an implementation of system 1200 for delivering sensory information to a subject mammal. The method 1500 comprises an operation s1502 to display a first stimulus in a first visual field on a first stimulus side of a subject, the first visual field being a right visual field or a left visual field of the subject. The method 1500 further comprises an operation s1504 to receive a first input from a first input side of the subject, the first input side being contralateral to the first stimulus side. The method 1500 further comprises an operation s1506 to display a second stimulus in a second visual field on a second stimulus side of the subject, the second visual field being the right visual field or the left visual field of the subject. The method 1500 further comprises an operation s1508 to receive a second input from a second input side of the subject, the second input side being ipsilateral to the second stimulus side. The method 1500 further comprises an operation s1510 to determine a crossed-uncrossed difference time as a difference between (i) a crossed reaction time comprising a first span of time between displaying the first stimulus and receiving the first input and (ii) an uncrossed reaction time comprising a second span of time between displaying the second stimulus and receiving the second input. The method 1500 further comprises an operation s1512 to determine a severity of a Traumatic Brain Injury of the subject. The method 1500 further comprises an operation s1514 to treat the subject based on the determined severity of Traumatic Brain Injury.

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as "an aspect" may refer to one or more aspects and vice versa. A phrase such as "an embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such "an embodiment" may refer to one or more embodiments and vice versa. A phrase such as "a configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as "a configuration" may refer to one or more configurations and vice versa.

Terms such as "top," "bottom," "front," "rear" and the like as used in this disclosure should be understood as referring to an arbitrary frame of reference, rather than to the ordinary gravitational frame of reference. Thus, a top surface, a bottom surface, a front surface, and a rear surface may extend upwardly, downwardly, diagonally, or horizontally in a gravitational frame of reference.

Furthermore, to the extent that the term "include," "have," or the like is used in the description or the claims, such term is intended to be inclusive in a manner similar to the term "comprise" as "comprise" is interpreted when employed as a transitional word in a claim.

The word "exemplary" is used herein to mean "serving as an example, instance, or illustration." Any embodiment described herein as "exemplary" is not necessarily to be construed as preferred or advantageous over other embodiments.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

While certain aspects and embodiments of the subject technology have been described, these have been presented by way of example only, and are not intended to limit the scope of the subject technology. Indeed, the novel methods and systems described herein may be embodied in a variety of other forms without departing from the spirit thereof. The accompanying claims and their equivalents are intended to cover such forms or modifications as would fall within the scope and spirit of the subject technology.

What is claimed is:

1. A method, comprising:
displaying a stimulus in a peripheral visual field at least 30 degrees from a fixation point on a stimulus side of a subject, the peripheral visual field being a right peripheral visual field or a left peripheral visual field of the subject;
receiving an input, comprising an indication that the subject perceived the stimulus, from an input side of the subject, the input side being contralateral to the peripheral visual field;
measuring a crossed reaction time comprising a span of time between displaying the stimulus and receiving the input;
based on the crossed reaction time, determining a severity of a traumatic brain injury of the subject; and
after the determining the severity of the traumatic brain injury of the subject, administering to the subject a treatment based on the determined severity of the traumatic brain injury, the treatment comprising at least one of administering a drug to the subject, performing a surgery on the subject, or applying a stimulus to the brain of the subject.

2. The method of claim 1, further comprising:

displaying a second stimulus in a second peripheral visual field at least 30 degrees from a fixation point on a second stimulus side of the subject, the second peripheral visual field being the right peripheral visual field or the left peripheral visual field of the subject;

receiving a second input, comprising an indication that the subject perceived the second stimulus, from a second input side of the subject, the second input side being ipsilateral to the second peripheral visual field;

measuring a crossed-uncrossed difference time as a difference between (i) the crossed reaction time and (ii) an uncrossed reaction time comprising a second span of time between displaying the second stimulus and receiving the second input; and based on the crossed-uncrossed difference time, further determining the severity of the traumatic brain injury of the subject.

3. The method of claim 1, wherein determining the severity of the traumatic brain injury comprises comparing the crossed reaction time of the subject to a crossed reaction time of a control subject not having a traumatic brain injury.

4. The method of claim 1, further comprising: outputting to an output device the determined severity of the traumatic brain injury.

5. The method of claim 1, further comprising: outputting to an output device a recommendation for the treatment for the administering.

\* \* \* \* \*